(12) United States Patent
Braun

(10) Patent No.: US 11,246,636 B2
(45) Date of Patent: Feb. 15, 2022

(54) SYSTEMS, METHODS, AND APPARATUS FOR SPINAL DEFORMITY CORRECTION

(71) Applicant: Cricket K. Braun and John T. Braun, MD Family LLC, Charlotte, VT (US)

(72) Inventor: John T. Braun, Charlotte, VT (US)

(73) Assignee: Braunvest LLC, Charlotte, VT (US)

( * ) Notice: Subject to any disclaimer, the term of this patent is extended or adjusted under 35 U.S.C. 154(b) by 164 days.

(21) Appl. No.: 16/601,471

(22) Filed: Oct. 14, 2019

(65) Prior Publication Data
US 2020/0337753 A1    Oct. 29, 2020

Related U.S. Application Data

(60) Provisional application No. 62/839,397, filed on Apr. 26, 2019.

(51) Int. Cl.
| | | |
|---|---|---|
| *A61B 17/86* | (2006.01) | |
| *A61B 17/70* | (2006.01) | |
| *A61B 17/04* | (2006.01) | |

(52) U.S. Cl.
CPC ...... *A61B 17/8635* (2013.01); *A61B 17/0401* (2013.01); *A61B 17/70* (2013.01); *A61B 17/7032* (2013.01); *A61B 17/864* (2013.01); *A61B 2017/044* (2013.01); *A61B 2017/0414* (2013.01)

(58) Field of Classification Search
CPC .... A61B 17/8635; A61B 17/864; A61B 17/70
See application file for complete search history.

(56) References Cited

U.S. PATENT DOCUMENTS

| | | |
|---|---|---|
| 5,387,213 A | 2/1995 | Breard et al. |
| 5,951,560 A | 9/1999 | Simon et al. |
| 6,299,613 B1 | 10/2001 | Ogilvie et al. |
| 7,285,121 B2 | 10/2007 | Braun et al. |
| 7,297,146 B2 | 11/2007 | Braun et al. |
| 7,691,131 B2 | 4/2010 | Graf |
| 7,727,258 B2 | 6/2010 | Graf |
| 7,845,945 B2 | 12/2010 | Canter |
| 8,172,880 B2 | 5/2012 | Graf |
| 8,177,810 B2 | 5/2012 | Ferree |
| 8,221,457 B2 | 7/2012 | Delecrin et al. |
| 8,641,736 B2 | 2/2014 | Marik et al. |
| 8,979,874 B2 | 3/2015 | Darois et al. |

(Continued)

FOREIGN PATENT DOCUMENTS

| | | |
|---|---|---|
| WO | WO2009128074 | 10/2009 |
| WO | WO2017127532 | 7/2017 |

*Primary Examiner* — Christian A Sevilla
(74) *Attorney, Agent, or Firm* — Matthew D. Thayne; Thayne and Davis LLC

(57) ABSTRACT

Bone anchors and related systems and elements, such as means for engaging a ligament to a bone anchor for correction of spinal deformities. In some embodiments, the bone anchor may be configured for engaging vertebral bone and may comprise an exterior thread form and an interior thread form, which may be positioned within an interior chamber of the bone anchor that may open at the distal end of the bone anchor where an outer thread form may also terminate. The inner chamber may taper in an opposite direction relative to an outer surface of the bone anchor upon which the outer thread form is positioned.

20 Claims, 16 Drawing Sheets

(56) References Cited

U.S. PATENT DOCUMENTS

| | | |
|---|---|---|
| 9,433,442 B2 | 9/2016 | Lindemann et al. |
| 9,833,230 B2 | 12/2017 | Stone |
| 10,179,015 B2 | 1/2019 | Lavigne et al. |
| 2002/0082598 A1 | 6/2002 | Teitelbaum |
| 2007/0292820 A1* | 12/2007 | Canter ................ A61C 8/0039 433/173 |
| 2010/0131010 A1 | 5/2010 | Graf |
| 2012/0189984 A1* | 7/2012 | Holmes ................ A61C 8/0022 433/174 |
| 2013/0253587 A1 | 9/2013 | Carls et al. |
| 2013/0304032 A1* | 11/2013 | Sardesai ............. A61B 17/864 604/522 |

* cited by examiner

SYSTEMS, METHODS, AND APPARATUS FOR SPINAL DEFORMITY CORRECTION

CROSS-REFERENCE TO RELATED APPLICATIONS

This application claims the benefit under 35 U.S.C. § 119(e) of U.S. Provisional Patent Application No. 62/839,397, which was filed Apr. 26, 2019 and titled "SYSTEMS, METHODS, AND APPARATUS FOR SPINAL DEFORMITY CORRECTION," which is hereby incorporated herein by reference in its entirety.

SUMMARY

Embodiments of apparatus and methods are disclosed herein that relate to correction and/or stabilization of spinal deformities, such as scoliosis. In some specific embodiments disclosed herein, such devices and/or systems may comprise bone anchors that may be particularly configured for coupling with vertebral bodies and that may be used in certain spinal surgeries, such as fusionless spinal surgeries that are often used to treat scoliosis and other similar deformities.

Existing bone anchors used for such procedures are typically configured to extend entirely through the vertebral bodies to provide for bicortical purchase. This is because the cortex portion of the vertebral body is viewed as the only portion of the bone with sufficient strength to hold the screw or other bone anchor in place while the corrective forces are being applied to the spinal column via a series of such screws/anchors. Inadequate screw purchase, such as purchase that terminates within the cancellous portion of the vertebra may therefore result in undesirable movement of the screw within the vertebral body, which may result in recurrence of the spinal deformity or at least decreased efficacy of the spinal correction system.

Other anchors have been developed, such as those disclosed in U.S. Pat. No. 7,285,121 titled "Devices and Methods for the Correction and Treatment of Spinal Deformities," which patent is incorporated herein by reference in its entirety. The anchors disclosed in this previous patent are shorter in length but wider to provide additional surface area for obtaining stable purchase in the cancellous bone without necessarily requiring bicortical purchase. However, the present inventor has improved upon this design by providing, in some embodiments, an inner chamber that is threaded, which may provide a number of benefits, such as drawing additional bone into the chamber, placing such bone under compression to accelerate healing and incorporation with the implant, and/or providing a differential in force and/or surface tension between various portions of the anchor, such as between the inner and outer surfaces of the implant, to further improve stability, healing, and/or provide other benefits.

Although the preferred embodiments disclosed herein are designed and configured for use in connection with spinal bones, such as vertebral bodies, the inventive principles disclosed herein may find application in other types of bones or even other types of tissues, particularly bones and/or tissues with similar characteristics to vertebral bones (i.e, largely cancellous bone/tissue and/or comprising an insufficient cortex). Examples of such alternative applications include suture anchors for rotator cuff repair and other similar surgical procedures, along with dental applications. It should be understood therefore that the bone anchors and other features/aspects disclosed herein may be used in connection with any bones, teeth, or other anatomical feature, including but not limited to those involving use of sutures and/or tethers for applying a force to such anatomical feature.

Thus, in a more specific example of a bone anchor, such as a bone anchor configured for vertebral attachment, the bone anchor may comprise an outer thread form that may be positioned on a tapered portion of the bone anchor. The bone anchor may further comprise an inner chamber, which may be located along the same portion along the primary axis of the bone anchor. The inner chamber may also comprise a thread form and/or may taper in an opposite direction. The inner and outer thread forms may differ from one another, such as by providing a larger thread depth on the thread form in the inner chamber, for example. Similarly, the inner and outer threads may differ in other aspects to increase the aforementioned force differential, such as by differing in thread direction/handedness, number of starts, angle, pitch diameter, major diameter, minor diameter, etc.

This may allow for increased fixation while increasing stimulation of bone ingrowth by increasing the forces that stimulate such bone growth. In other words, by providing an inner chamber that has threads and/or tapers, as described herein, bone may be inserted into and compacted within the chamber as the anchor is advanced. Although providing a tapered chamber or a chamber that otherwise decreases in volume from the distal end towards the proximal end is preferred, some such benefits may be provided by providing a cylindrical chamber comprising internal threads.

In some embodiments, the bone anchor may further comprise an engagement member or other means for engaging a ligament to impart a force to a vertebral body or other tissue or anatomical feature. Such engagement member or other feature may be incorporated directly into the bone anchor or may be part of a cap or other such element that may be coupled with the bone anchor. In some embodiments, the engagement member or engagement means and/or a cap or the like to which the engagement member/means is coupled may be rotatable with respect to the thread form(s) of the anchor to allow for selective repositioning of the engagement member/means following insertion of the bone anchor into a vertebral body or other bone or body tissue.

In a more specific example of a bone anchor, such as a bone screw or other bone anchor, configured for engagement with a vertebral body or other bone, the anchor may comprise a first section comprising an at least substantially conical shape in cross section and a second section comprising an at least substantially cylindrical shape in cross section. The second section may be positioned distal of the first section and may form a tip of the bone anchor. The bone anchor may further comprise an inner chamber. An outer thread form may be formed on an outer surface of the bone anchor and an inner thread form may be formed on an inner surface of the bone anchor within the inner chamber.

Some embodiments may further comprise a third section, which may comprise a cross-sectional width in a direction at least substantially perpendicular to an elongated axis of the bone anchor. The cross-sectional width may be maximal between opposing ends of the third section. In some such embodiments, the third section may comprise an outer surface having a convex, curved shape. The third section may be positioned in between the first section and the second section.

In some embodiments, the third section may comprise an outer thread form, which may, in some embodiments, begin at or at least substantially at a point of maximal width of the third section.

In some embodiments, the inner thread form may differ from the outer thread form so as to provide a differential in force between forces generated by the outer thread form on vertebral bone adjacent to the outer thread form and forces generated by the inner thread form on vertebral bone within the inner chamber.

In some embodiments, the second section may lack outer threads. In some embodiments, the second section may also, or alternatively, lack inner threads. The second section and/or distal most end of the bone anchor may comprise a sharp edge configured to facilitate penetration into a vertebral body.

In another example of a threaded bone anchor configured for engagement with a vertebral body, the anchor may comprise a tapered section comprising an outer thread form and an inner chamber comprising an inner thread form. The inner chamber may comprise a proximal end and a distal end and may taper or otherwise decrease in size, at least in part, between the distal end and the proximal end. The inner thread form may differ from the outer thread form so as to provide a differential in force between forces generated by the outer thread form on vertebral bone adjacent to the outer thread form and forces generated by the inner thread form on vertebral bone within the inner chamber, such as by differing in one or more of thread depth, thread direction, number of starts, angle, pitch diameter, major diameter, taper angle, and minor diameter. As a more specific example, in some embodiments, the inner thread form may comprise a larger thread depth than the outer thread form. Any of the aforementioned threads may be partial and/or transition along the thread form as well, if desired.

In some embodiments, the inner chamber may taper, in part or in whole, from a proximal portion of the bone anchor to a distal portion of the bone anchor to define a wider bone anchor width at a proximal portion of a tapering section of the bone anchor than at a distal portion of the tapering section.

Some embodiments may further comprise a non-tapered section positioned at a distal end of the bone anchor, such as a portion having a cylindrical shape in cross section. In some embodiments, the non-tapered section may lack threads and/or comprise a sharp distal edge to facilitate bone penetration.

In an example of a bone anchor configured for engagement with a vertebral body according to other embodiments, the bone anchor may comprise an outer surface configured to engage vertebral bone and extending along a longitudinal axis of the bone anchor. The outer surface may taper, at least in part, from a proximal portion of the bone anchor to a distal portion of the bone anchor to define a wider bone anchor width at a proximal portion of a tapering section of the bone anchor than at a distal portion of the tapering section. The bone anchor may further comprise an inner chamber configured to engage and compact vertebral bone therein. The inner chamber may taper in a direction opposite a direction in which the outer surface tapers such that at least a portion of the inner chamber is wider at a distal portion of the inner chamber than an adjacent proximal portion of the inner chamber.

In some embodiments, the inner chamber may comprise an inner thread form and/or the outer chamber may comprise an outer thread form. In some embodiments, the inner thread form of the inner chamber may differ from the outer thread form of the outer chamber so as to provide a differential in force between forces generated by the outer thread form on vertebral bone adjacent to the outer thread form and forces generated by the inner thread form on vertebral bone within the inner chamber.

Some embodiments may further comprise a cylindrical section, which may, in some embodiments, form a distal tip of the bone anchor configured to facilitate penetration into a vertebral body.

The features, structures, steps, or characteristics disclosed herein in connection with one embodiment may be combined in any suitable manner in one or more alternative embodiments.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

Figure 1A:
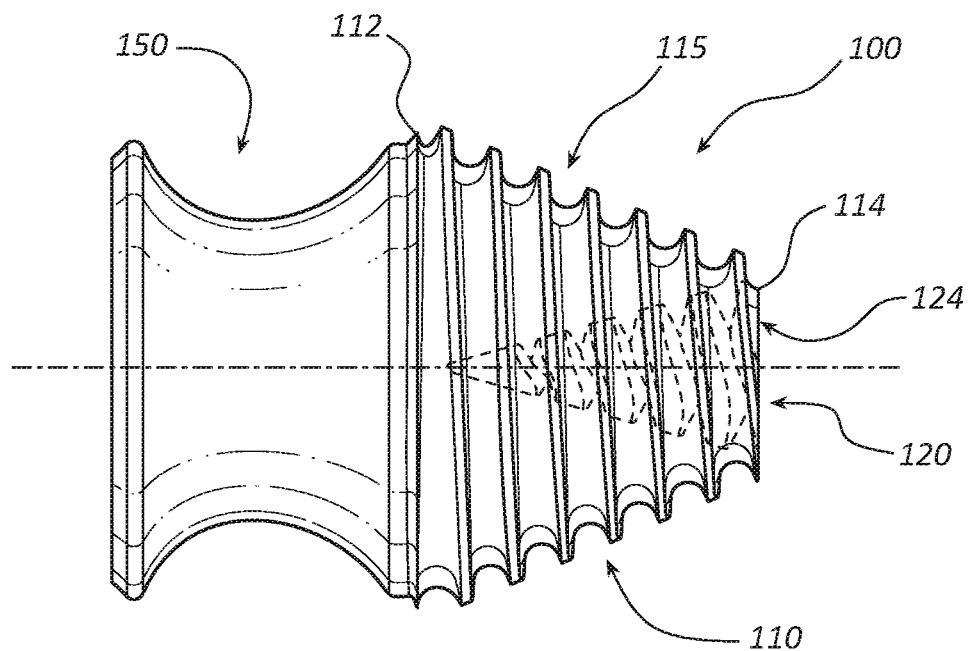
FIG. 1A is a perspective view of a vertebral bone anchor according to some embodiments.

It will be readily understood that the components of the present disclosure, as generally described and illustrated in the drawings herein, could be arranged and designed in a wide variety of different configurations. Thus, the following more detailed description of the embodiments of the apparatus is not intended to limit the scope of the disclosure but is merely representative of possible embodiments of the disclosure. In some cases, well-known structures, materials, or operations are not shown or described in detail.

As used herein, the term "substantially" refers to the complete or nearly complete extent or degree of an action, characteristic, property, state, structure, item, or result to function as indicated. For example, an object that is "substantially" cylindrical or "substantially" perpendicular would mean that the object/feature is either cylindrical/perpendicular or nearly cylindrical/perpendicular so as to result in the same or nearly the same function. The exact allowable degree of deviation provided by this term may depend on the specific context. The use of "substantially" is equally applicable when used in a negative connotation to refer to the complete or near complete lack of an action, characteristic, property, state, structure, item, or result. For example, structure which is "substantially free of" a bottom would either completely lack a bottom or so nearly completely lack a bottom that the effect would be effectively the same as if it completely lacked a bottom.

Similarly, as used herein, the term "about" is used to provide flexibility to a numerical range endpoint by providing that a given value may be "a little above" or "a little below" the endpoint while still accomplishing the function associated with the range.

The embodiments of the disclosure may be best understood by reference to the drawings, wherein like parts may be designated by like numerals. It will be readily understood that the components of the disclosed embodiments, as generally described and illustrated in the figures herein, could be arranged and designed in a wide variety of different configurations. Thus, the following detailed description of the embodiments of the apparatus and methods of the disclosure is not intended to limit the scope of the disclosure, as claimed, but is merely representative of possible embodiments of the disclosure. In addition, the steps of a method do not necessarily need to be executed in any specific order, or even sequentially, nor need the steps be executed only once, unless otherwise specified. Additional details regarding certain preferred embodiments and implementations will now be described in greater detail with reference to the accompanying drawings.

Figure 1B:
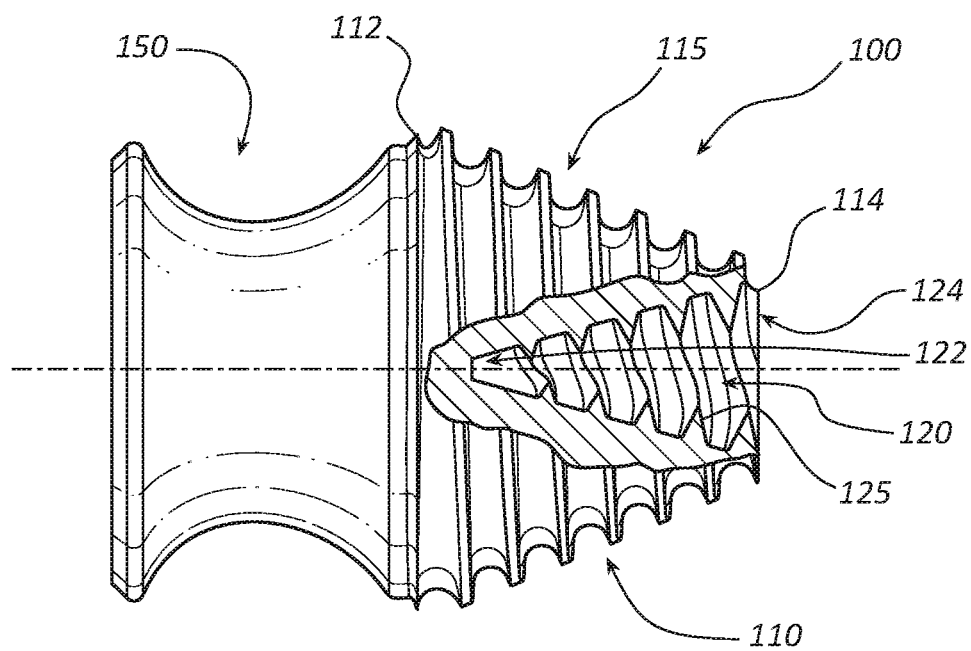
FIG. 1B is a cutaway, perspective view of the vertebral bone anchor of FIG. 1A.

FIGS. 1A and 1B depict an example of a bone anchor or implant 100 according to some embodiments. Bone anchor 100 comprises a bone engagement portion 110 that comprises an exterior surface that is tapered from the proximal end 112 to the distal end 114 such that the distal end 114 is narrower than the proximal end 112. In preferred embodiments, the angle of this taper may range from about 1 degree to about 20 degrees. In some such embodiments, the angle of this taper may range from about 5 degrees to about 10 degrees. In some embodiments, the exterior surface of the bone engagement portion of bone anchor 100 may define a conical or frusto-conical shape.

The exterior surface of bone engagement portion 110 further comprises a thread form 115, such as preferably a thread form having a relatively wide and/or deep thread configured for engagement with cancellous bone, such as the cancellous bone inside the cortical wall of a vertebrae. As discussed and, in some cases, depicted in connection with embodiments referenced below, such thread form 115 may comprise any suitable thread form, such as a single thread, a dual-lead thread, a triple-lead thread, and the like. As also discussed in greater detail below, in some embodiments, thread form 115 may vary throughout the form, such as by increasing and/or decreasing in pitch or depth from the proximal end 112 to the distal end 114.

Bone anchor 100 further comprises an inner chamber 120. Inner chamber 120 may be defined by an inner surface that, like the outer surface of bone engagement portion 110, also tapers. However, in preferred embodiments, inner chamber 120 tapers in the opposite direction relative to the outer surface of bone engagement portion 110. Thus, as shown in the cutaway view of FIG. 1B, chamber 120 tapers from its proximal end 122 to its distal end 124, which distal end 124 coincides with the distal end 114 of the entire bone engagement portion 110 in the depicted embodiment, such that the proximal end 122 of the inner chamber 120 is smaller in diameter and/or another suitable dimension than the distal end 124 of chamber 120. In preferred embodiments, the angle of this inner taper to chamber 120 may range from about 1 degree to about 20 degrees. In more preferred embodiments, the angle of this inner taper to chamber 120 may range from about 5 degrees to about 10 degrees.

Preferably, the length of the inner chamber 120 is greater than about 50% of the length of bone engagement portion 110 and/or thread form 115. In some embodiments, the length of the inner chamber 120 may be between about 30% and about 100% of the length of bone engagement portion 110 and/or thread form 115. In some such embodiments, the length of the inner chamber 120 may be between about 50% and about 80% of the length of bone engagement portion 110 and/or thread form 115.

Inner chamber 120 is preferably configured to do one or more of actively engage and draw bone or other tissue into chamber 120, provide a differential in force and/or surface tension between the inner and outer surfaces of the implant, and compress the bone/tissue as it is being drawn into the chamber 120. The reverse taper of the inner chamber 120 previously discussed may provide for compression of the bone/tissue as it is introduced into the chamber by threading the exterior thread form 115 into the bony tissue.

As another possible feature that may serve to actively engage and draw bone or other tissue into chamber 120 and/or provide a differential in force and/or surface tension between the inner and outer surfaces of the implant 100, chamber 120 preferably also comprises a thread form 125. As with external thread form 115, internal thread form 125 may comprise any suitable thread form, such as a single thread, a dual-lead thread, a triple-lead thread, etc., and may vary along the form, such as by increasing and/or decreasing in pitch or depth from the proximal end 122 to the distal end 124. Internal thread form 125, along with any of the other similar thread forms disclosed herein, may terminate prior to the proximal end of the chamber 120 so as to provide an unthreaded chamber at the end. Similarly, the internal thread form 125 may vary from one location to another, such as by providing a tapering thread form, reversing direction, increasing or decreasing in depth, pitch, etc. For example, the internal thread form may, similar to the internal vs. external thread forms, comprise opposing forces and/or adjacent features that are opposed to one another to enhance bone compaction and/or provide other benefits.

In particularly preferred embodiments, thread form 115 may differ from thread form 125, which may further contribute to one or more of these features to improve functionality. For example, thread form 125 may comprise a different pitch, a different depth, a different number of leads, and/or a different thread type relative to thread form 115. Other examples are providing a thread form 125 that varies in pitch and/or depth in a different direction, or to a different degree, relative to thread form 115. Again, this differential may contribute to a differential in force and/or tension that may improve bone healing, anchor stability, and/or provide other improvements. Although providing internal thread form 125 is preferred for these purposes, it is contemplated that, in alternative embodiments, inner chamber 120 may instead comprise other surface features, such as spikes, barbs, or other protrusions, grooves, and/or the like, that are configured to engage and/or draw in bone or other tissue. In some embodiments general surface roughening may even be useful for one or more of these purposes.

In certain preferred embodiments, thread form 125 has a greater thread depth along at least a portion of the thread form 125 (in some such embodiments, along the entire thread form 125) than the thread depth along at least a portion of thread form 115 (again, in some embodiments, along the entire thread form 115). In some such embodiments, for example, the depth of thread form 125 may be, along at least a portion thereof, between about 5 and about 50% greater than the depth of thread form 115 along at least a portion thereof. The depth of thread form 125 may vary, for example, between about 1 and about 5 mm in some embodiments.

Anchor 100 further comprises an engagement member 150 positioned at its proximal end. Engagement member 150 in the depicted embodiment comprises an annular groove that may be configured to engage a ligament or other flexible member that may also engage another anchor (not shown) to span multiple vertebrae and allow for introduction of a correctional force for correction of scoliosis or another spinal deformity. Of course, the annular groove shown in FIGS. 1A and 1B may be replaced with any of a variety of other engagement members available to those of ordinary skill in the art that would allow for application of a force between two or more anchors to apply such a correctional force using a ligament, rod, or other coupling member. Examples of such alternative engagement members include a tulip, clamp, post, hole, slot, and the like, some of which are discussed below in connection with other figures. Any of these engagement members, including engagement member 150, should be considered examples of means for engaging a ligament to impart a force to a vertebral body or other tissue or anatomical feature.

Figure 2A:
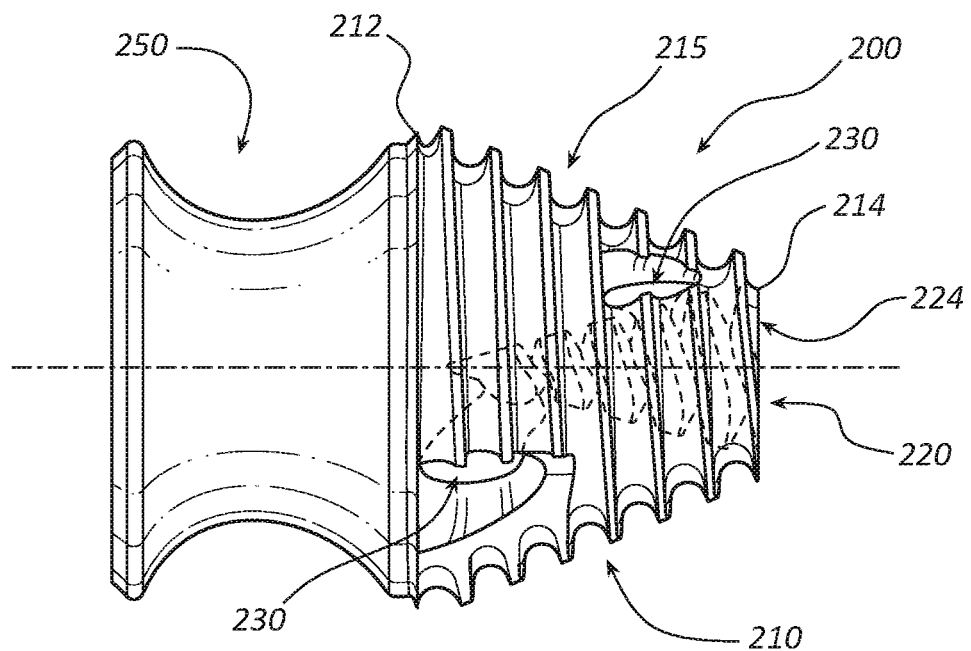
FIG. 2A is a perspective view of a vertebral bone anchor according to other embodiments.
Figure 2B:
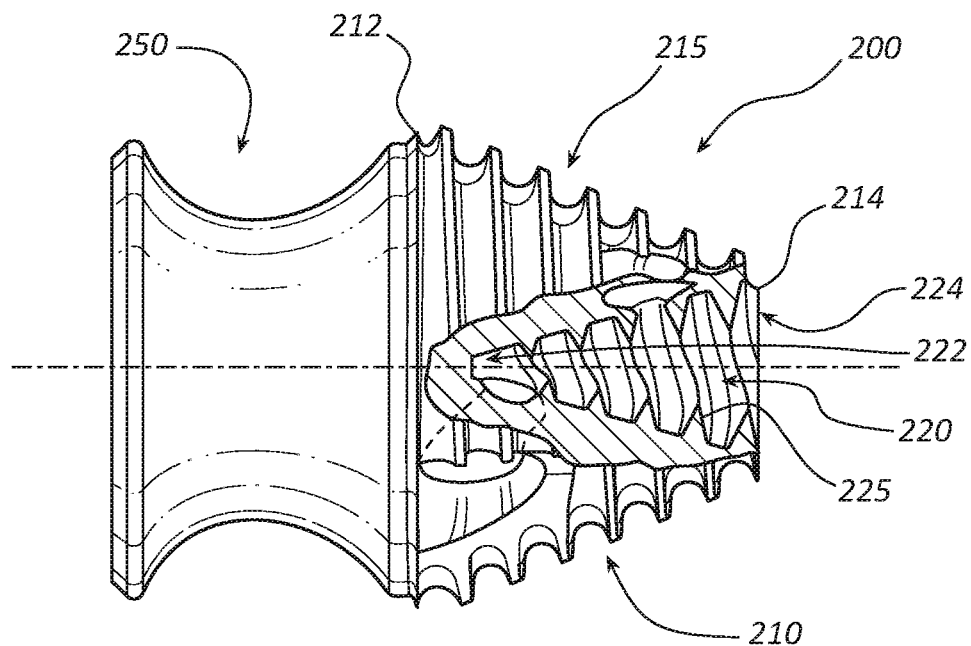
FIG. 2B is a cutaway, perspective view of the vertebral bone anchor of FIG. 2A.

FIGS. 2A and 2B depict another embodiment of an anchor 200. Like anchor 100, anchor 200 comprises a bone engagement portion having an exterior surface that is tapered from the proximal end 212 to the distal end 214 such that the distal end 214 is narrower than the proximal end 212. Similarly, the exterior surface of bone engagement portion further comprises a thread form 215. Again, in some embodiments, thread form 215 may vary throughout the form, such as by increasing and/or decreasing in pitch or depth from the proximal end 212 to the distal end 214.

Bone anchor 200 also further comprises an inner chamber 220 defined by an inner surface that tapers, preferably in an opposite direction relative to the outer surface of the bone engagement portion of anchor 200. The other dimensions, configurations, and options referenced above in connection with bone anchor 100 may also apply to bone anchor 200.

Thus, once again, inner chamber 220 is preferably configured to do one or more of actively engage and draw bone or other tissue into chamber 220, provide a differential in force and/or surface tension between the inner and outer surfaces of the anchor 200, and compress the bone/tissue as it is being drawn into the chamber 220, which may be accomplished by the reverse taper of the inner chamber and/or the internal thread form 225. As with thread forms 115/125, thread form 215 may differ from thread form 225, which may further contribute to one or more of these features to improve functionality.

In some embodiments, it may be desirable to create a force differential along one or more of the thread forms, such as, for example, by providing an external thread form that differs in pitch or otherwise along the length of the thread form. Similarly, it may be desirable to provide a force differential along the internal thread form by, for example, altering the internal thread form, by way of pitch, depth, etc., from one end of the thread form to the other, or by providing distinct, spaced apart thread forms on the inner and/or outer surfaces of the implant.

Anchor 200 further comprises an engagement member 250 defining an annular groove that may be configured to engage a ligament or other flexible member that may also engage another anchor (not shown) to span multiple vertebrae and allow for introduction of a correctional force for correction of scoliosis or another spinal deformity.

Unlike anchor 100, however, anchor 200 comprises a plurality of tunnels 230 and/or openings that extend from the exterior surface of anchor 200 to the inner chamber 220. These tunnels 230 may comprise sharpened and/or beveled edges to further facilitate drawing of bone material into chamber 220 as anchor 200 is advanced through a vertebral body.

Figure 3A:
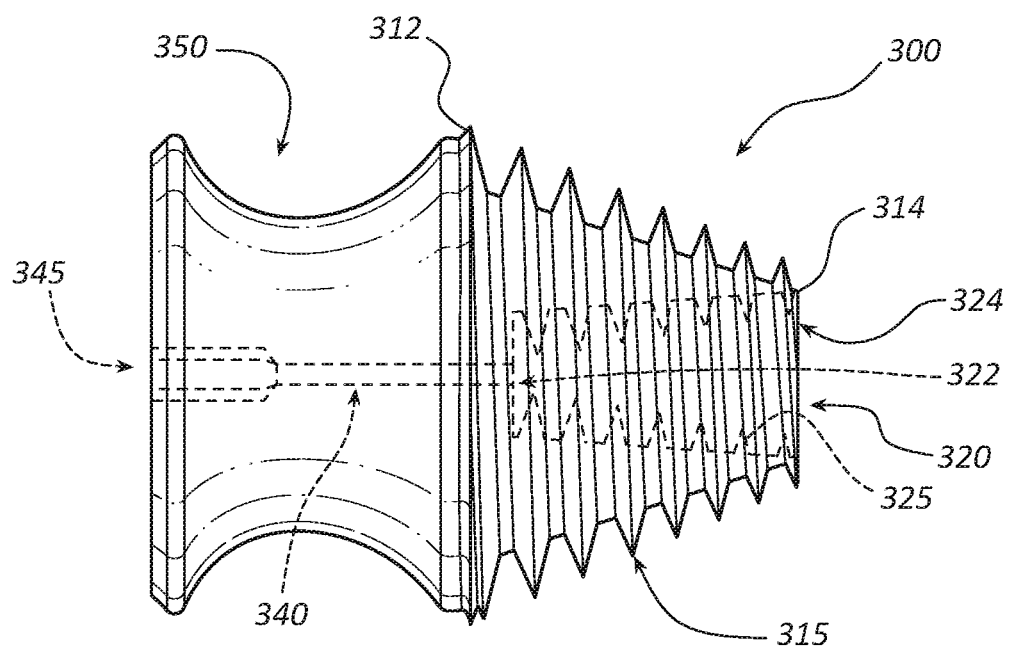
FIG. 3A is a perspective view of a vertebral bone anchor according to still other embodiments.

FIG. 3A depicts another embodiment of an anchor 300. Like anchors 100 and 200, anchor 300 again comprises a bone engagement portion comprising a thread form 315 and having an exterior surface that is tapered from the proximal end 312 to the distal end 314 such that the distal end 314 is narrower than the proximal end 312. Again, in some embodiments, thread form 315 may vary throughout the form, such as by increasing and/or decreasing in pitch or depth from the proximal end 312 to the distal end 314.

Bone anchor 300 also comprises an inner chamber 320 defined by an inner surface that tapers, preferably in an opposite direction relative to the outer surface of bone engagement portion. Chamber 320 is shown having a wider proximal end 322 than bone anchors 100 and 200. The other dimensions, configurations, and options referenced above in connection with bone anchors 100 and 200 may also apply to bone anchor 300.

Thus, once again, inner chamber 320 is preferably configured to do one or more of actively engage and draw bone or other tissue into chamber 320, provide a differential in force and/or surface tension between the inner and outer surfaces of the anchor 300, and compress the bone/tissue as it is being drawn into the chamber 320, which may be accomplished by the reverse taper of the inner chamber and/or the internal thread form 325. Once again, thread form 315 also preferably differs from thread form 325, which may further contribute to one or more of these features to improve functionality.

Anchor 300 further comprises an engagement member 350 defining an annular groove that may be configured to engage a ligament or other flexible member that may also engage another anchor (not shown) to span multiple vertebrae and allow for introduction of a correctional force for correction of scoliosis or another spinal deformity.

Unlike anchors 100 and 200, anchor 300 further comprises a channel 340 or cannulation that terminates in the proximal end of anchor 300. Channel 340 may be configured to receive a tool or portion of a tool and may facilitate introduction/implantation of anchor 300, such as a probe or guidewire. Thus, channel 340 may extend into chamber 320 so that a tunnel, which may be defined in part by channel 340 and in part by chamber 320, extends through the entire length of anchor 300 along its axis. In the depicted embodiment, a keyed tool recess 345 may be formed along the proximal portion of channel 340, which may be configured to receive a driver or other keyed male instrument for rotation/driving of anchor 300. Of course, in other embodiments, channel 340 need not extend the full length of anchor 300.

Figure 3B:
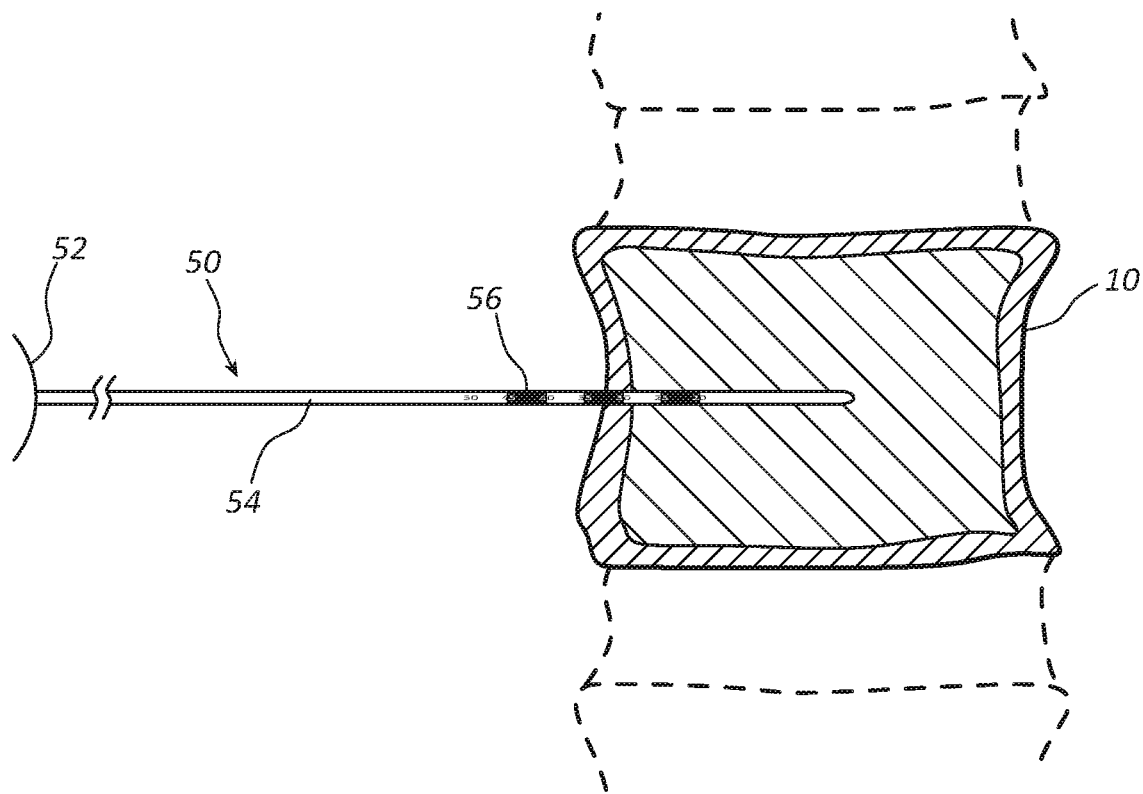
FIG. 3B is a cross-sectional view of a vertebral probe preparing a vertebral body for receipt of a bone anchor therein.

A preferred methodology for installing anchor 300 is depicted in FIGS. 3B-3E. Thus, as shown in FIG. 3B, a probe 50 may initially be inserted through the cortical wall of vertebral body 10 to establish a preferred path for insertion of anchor 300 therein. Probe 50 may comprise a handle or head 52 that, in some embodiments, may be removable from the shaft 54 of probe 50. In some such embodiments, head 52 may be slidably received over the proximal end of shaft 54 to allow for application of a distal force to insert probe 50 through the proximal cortical wall of vertebrae 10 but then allow for removal of head 52 by withdrawing head 52 proximally. In some embodiments, probe 50 may comprise a tip and/or other feature described in U.S. Provisional Patent Application No. 62/712,158, which was filed on Jul. 30, 2018 and titled "Vertebral Probes and Related Surgical Methods," which is hereby incorporated by reference herein in its entirety.

Shaft 54 may comprise a series of markings 56 configured to further facilitate ease of use, safety, and/or subsequent screw/anchor placement. More particularly, shaft 54 may comprise a series of alternating markings 56, which may include alphanumerical markings, dash lines, colors, patterns, etc. In some embodiments, a series of adjacent sections comprising distinct markings of one or more types may be provided. By varying the sections in this manner, a surgeon may be provided with a more general view, once the surgeon becomes familiar with the marking system, of the probe 50 placement without having to rely on specific alphanumerical markings. Of course, those of ordinary skill in the art will appreciate a variety of alternative configurations to allow a surgeon to visualize an approximate location of a vertebral probe within a vertebral body without requiring precise numerical measurements and/or tick marks/dash lines.

Figure 3C:
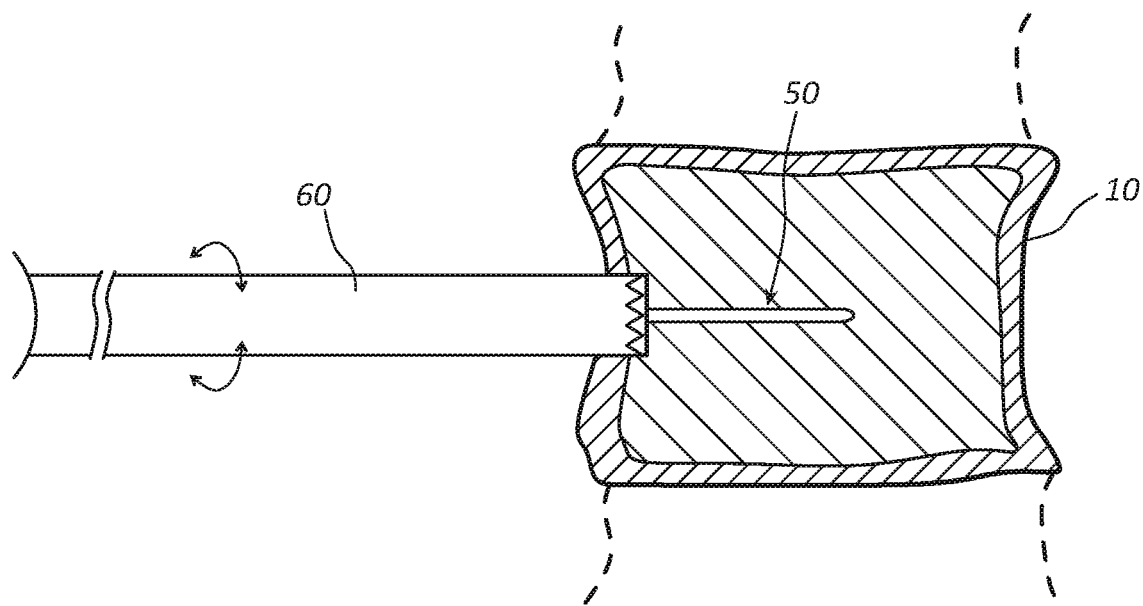
FIG. 3C is a cross-sectional view of a tap that may be slidably received over the vertebral probe or a guidewire to create a starter hole and/or otherwise further prepare the vertebral body for receipt of the bone anchor.

After establishing a desired path within vertebrae 10, head 52 may be removed and, in some embodiments and implementations, a secondary tool, such as a bone screw tap 60 comprising a central opening configured to receive shaft 54 of probe 50, may be inserted over probe 50. Tap 60 or another suitable instrument may comprise a distal end having a series of teeth, spikes, threads, or the like to create a divot or starter hole to facilitate insertion of the anchor 300, as shown in FIG. 3C. In some embodiments, the instrument may comprise a rounded tip, a beveled tip, or a tip having a sharp and/or pointed distal end.

Figure 3D:
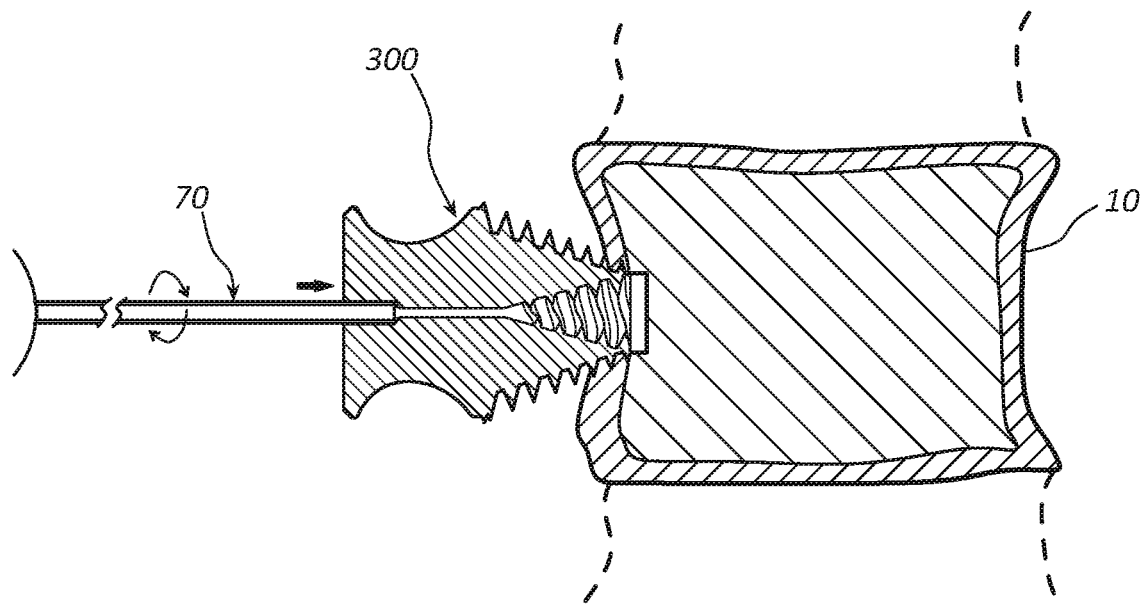
FIG. 3D is a cross-sectional view of the bone anchor of FIG. 3A being inserted into the vertebral body.
Figure 3E:
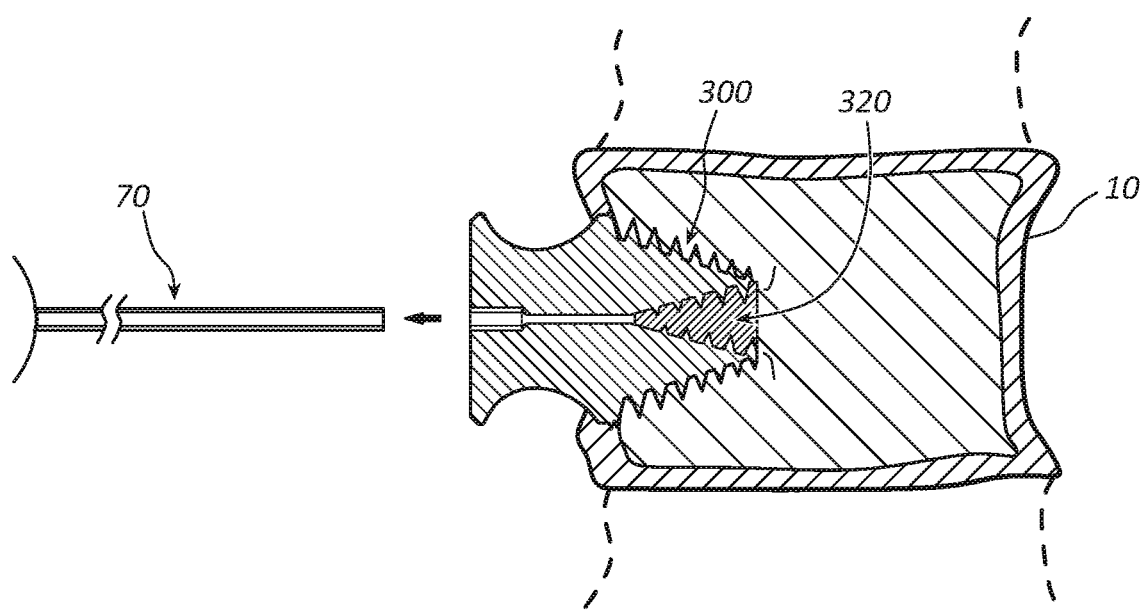
FIG. 3E is a cross-sectional view following insertion of the bone anchor of FIG. 3A into the vertebral body.

Following sufficient preparation of receipt for anchor 300, bone screw tap 60 may be removed from probe 50 (or a guidewire) and anchor 300 may be advanced into place adjacent to the prepared bone entry site over probe 50 or a guidewire (not shown). As shown in FIG. 3D, anchor 300 may then be rotated and/or driven into the vertebrae 10. In some embodiments and implementations, probe 50 may comprise a keyed portion configured to engage keyed recess 345 of anchor 300 such that this device may also be used to drive the anchor. Alternatively, another driver or suitable device may be used for this purpose, such as driver 70 shown in FIG. 3D. Thus, in some embodiments and implementations, probe 50 may be removed prior to advancing anchor 300. As shown in FIG. 3E, as implant 300 is driven into vertebrae 10, bone is received and automatically compacted within chamber 320 due to the features previously discussed, including the reverse taper of chamber 320.

Figure 4A:
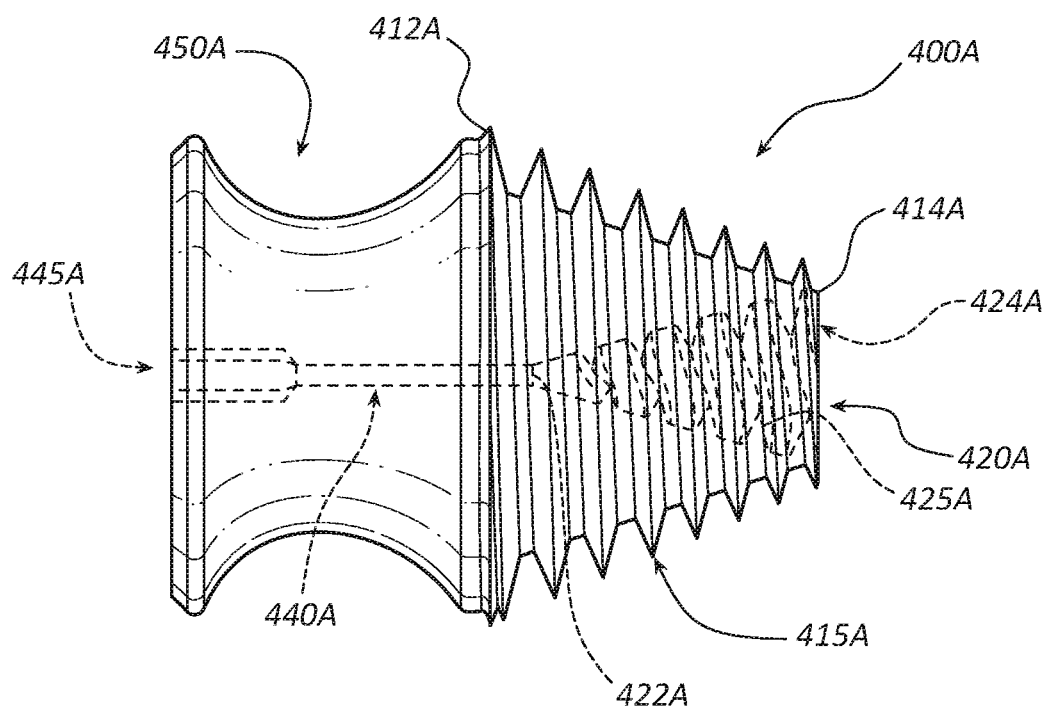
FIG. 4A is a perspective view of a vertebral bone anchor according to still other embodiments.
Figure 4B:
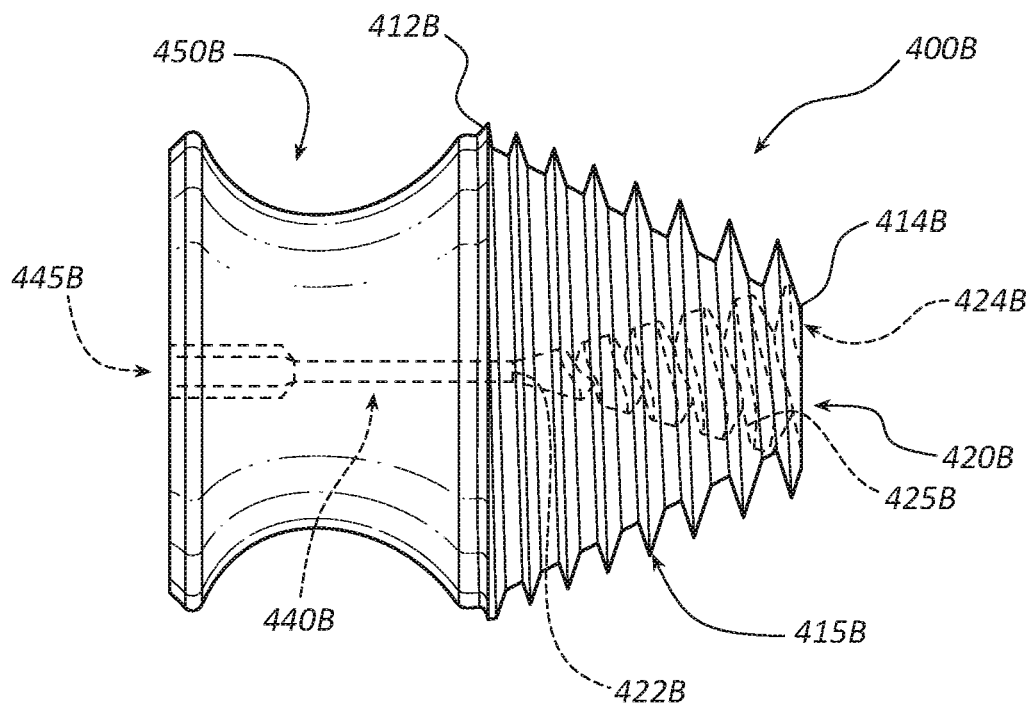
FIG. 4B is a perspective view of a vertebral bone anchor according to further embodiments.

Still other embodiments of bone anchors are shown in FIGS. 4A and 4B at 400A and 400B, respectively. Bone anchors 400A and 400B are similar to the previous bone anchors discussed in connection with previous figures except thread forms 415A/415B gradually differ in thread depth between the proximal ends 412A/412B and the distal ends 414A/414B of their respective anchor. More particularly, thread form 415A defines a thread depth that decreases from the proximal end 412A to the distal end 414A and thread form 415B defines a thread depth than increases from the proximal end 412B to the distal end 414B.

These bone anchors 400A/400B are otherwise similar to the anchors previously discussed and may include, or be modified to omit, any of the features discussed in connection with such anchors. Thus, bone anchors 400A/400B both comprise an inner chamber 420A/420B that preferably tapers in the opposite direction as the exterior surface of the bone engagement portion of the anchor 400A/400B upon which the thread forms 415A/415B are formed such that the proximal portions 422A/422B are smaller in diameter or another dimension than the distal portions 424A/424B, as previously mentioned. In addition, bone anchors 400A/400B further comprise respective second thread forms 425A/425B within chambers 420A/420B, engagement members 450A/450B for engaging ligaments or other engagement bands, a central cannulation 440A/440B, and a keyed feature 445A/445B to facilitate engagement with a driver or other suitable instrument for driving the anchor into a vertebral body or other tissue.

Figure 5A:
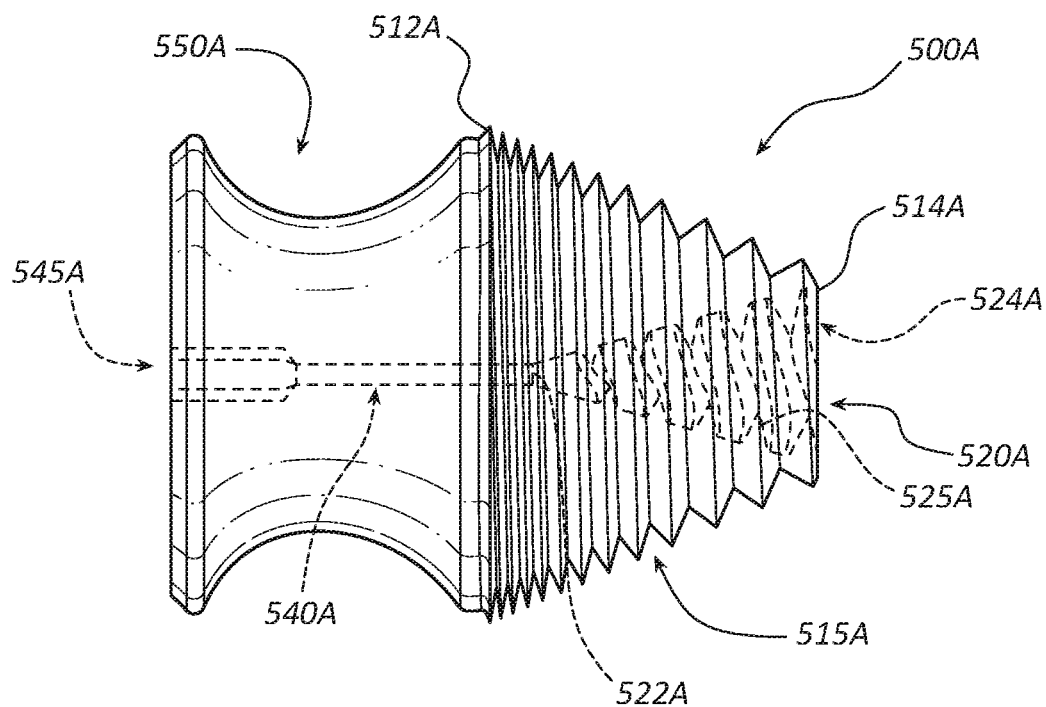
FIG. 5A is a perspective view of a vertebral bone anchor according to still further embodiments.
Figure 5B:
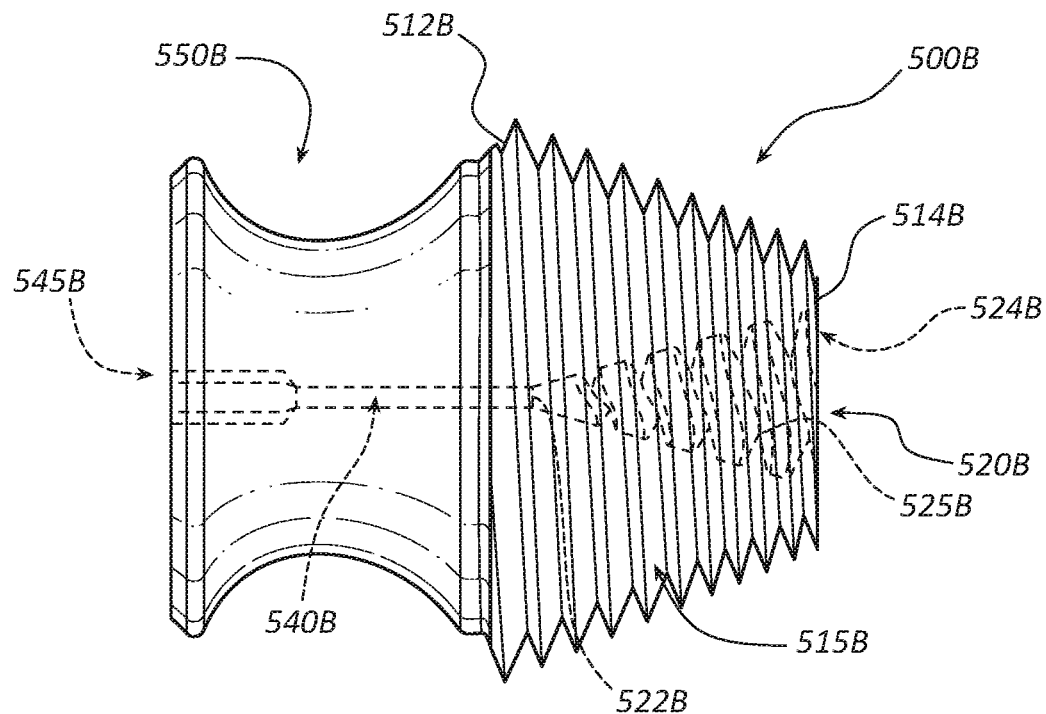
FIG. 5B is a perspective view of a vertebral bone anchor according to additional embodiments.

Additional embodiments of bone anchors are shown in FIGS. 5A and 5B at 500A and 500B, respectively. Once again, bone anchors 500A and 500B are similar to the previous bone anchors depicted except thread forms 515A/515B gradually differ in thread pitch between the proximal ends 512A/512B and the distal ends 514A/514B of a bone engagement region of their respective anchor. More particularly, thread form 515A defines a thread pitch that increases from the proximal end 512A to the distal end 514A and thread form 515B defines a thread pitch than decreases from the proximal end 512B to the distal end 514B.

These bone anchors 500A/500B are otherwise similar to the anchors previously discussed and may include, or be modified to omit, any of the features discussed in connection with such anchors. Thus, bone anchors 500A/500B both comprise an inner chamber 520A/520B that preferably tapers in the opposite direction as the exterior surface of the bone engagement portion of the anchor 500A/500B upon which the thread forms 515A/515B are formed. In addition, bone anchors 500A/500B further comprise respective second, internal thread forms 525A/525B within chambers 520A/520B. These internal thread forms 525A/525B preferably differ in one or more ways relative to external thread forms 515A/515B, such as by providing an increased thread depth, differing pitch, etc. The internal thread forms 525A/525B may also vary between their respective proximal and distal ends, similar to the external thread forms 515A/515B.

Bone anchors 500A/500B further comprise engagement members 550A/550B for engaging ligaments or other engagement bands, a central cannulation 540A/540B, and a keyed feature 545A/545B to facilitate engagement with a driver or other suitable instrument for driving the anchor into a vertebral body or other tissue.

Figure 6:
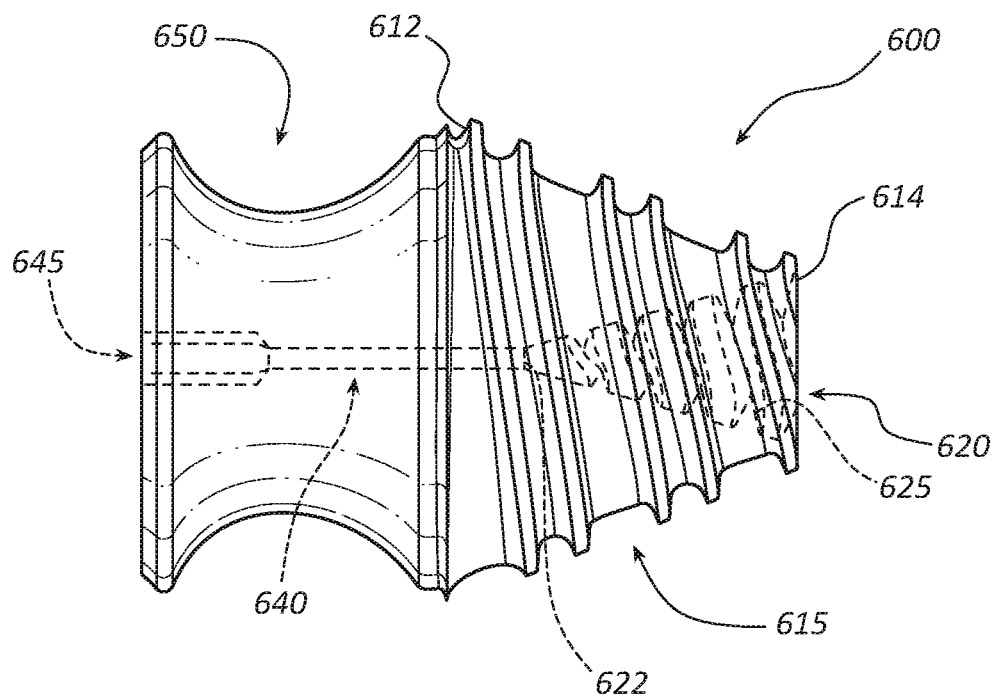
FIG. 6 is a perspective view of a vertebral bone anchor according to still other embodiments.

Yet another alternative embodiment of a bone anchor 600 is depicted in FIG. 6. Bone anchor 600 comprises an external thread form 615 that comprises a dual-lead thread form. Other embodiments may comprise a triple lead thread form. Again, one or more of the previously described features may be included as desired, including an internal chamber 620 comprising an internal thread form 625. Internal thread form 625 may comprise a single, double, or triple lead thread form, or any other suitable thread form. Again, in certain preferred embodiments, internal thread form 625 may differ from external thread form 625 in one or more ways in order to provide a differential in force and/or surface tension between various portions of the anchor 600, such as between the inner and outer surfaces of the implant 600. In the depicted embodiment, anchor 600 further comprises an engagement member 650, a central cannulation for a guide wire, probe, or other instrument, and a keyed feature 645.

Figures 7A, 7B:
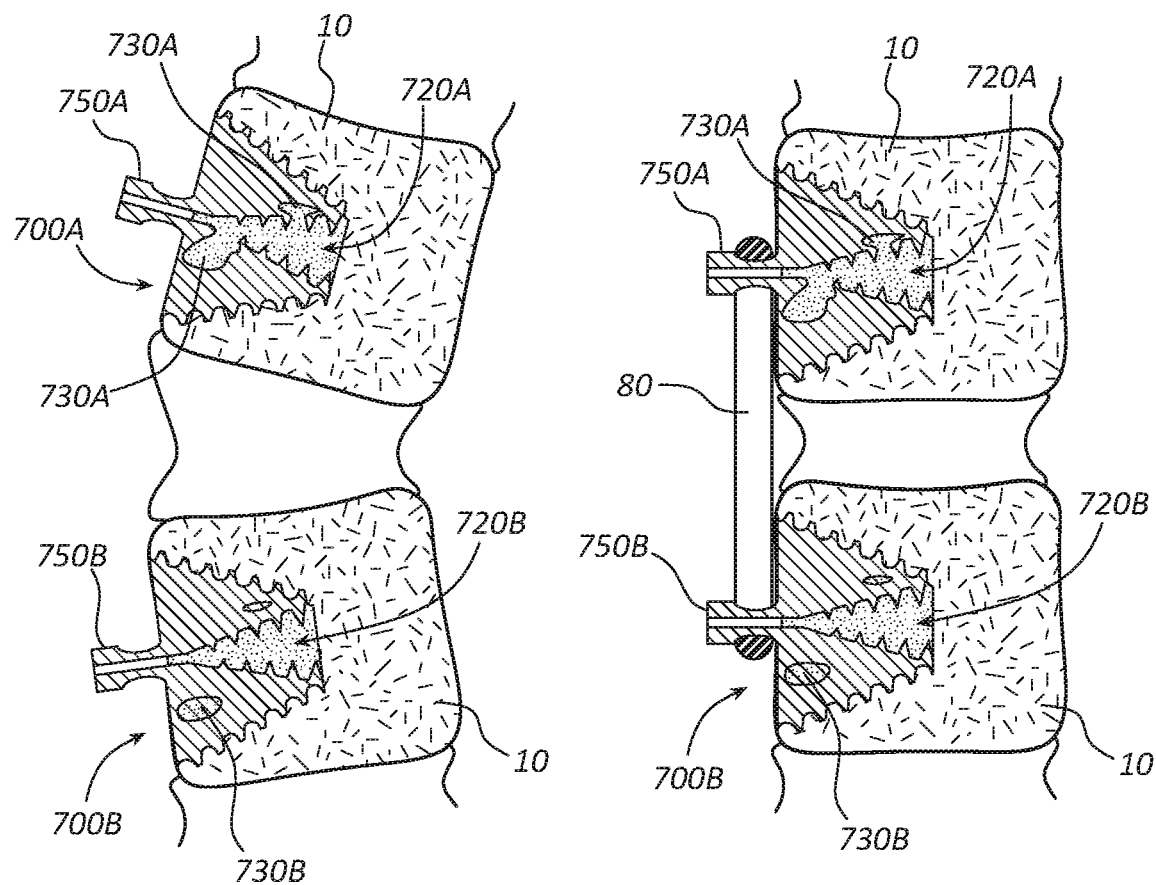
FIG. 7A is a cross-sectional view of a system for spinal deformity correction according to some embodiments shown prior to application of a restorative force via ligaments.
FIG. 7B is a cross-sectional view of a system for spinal deformity correction according to some embodiments shown following application of a restorative force via ligaments.

FIGS. 7A and 7B depict a system for spinal deformity correction comprising two bone anchors 700A/700B each coupled with an adjacent vertebral body 10. As those of ordinary skill in the art will appreciate, any number of bone anchors may be used as desired in accordance with the particular surgical procedure being performed. As shown in FIG. 7B, a loop ligament 80 may be wrapped around respective engagement members 750A/750B of the adjacent anchors 700A/700B to apply a restorative force to a patient's spinal column. Various additional elements, features, and/or methods may be used to increase and/or decrease this force as needed, some of which are discussed below.

As also shown in these figures, bone anchors 700A/700B may each comprise one or more tunnels 730A/730B that may allow for driving additional bone material into inner chambers 720A/720B, as previously described. These tunnels 730A/730B may also allow for an outlet to the pressure that may build up within chambers 720A/720B as bone anchors 700A/700B are driven through the vertebral bone.

Figure 8:
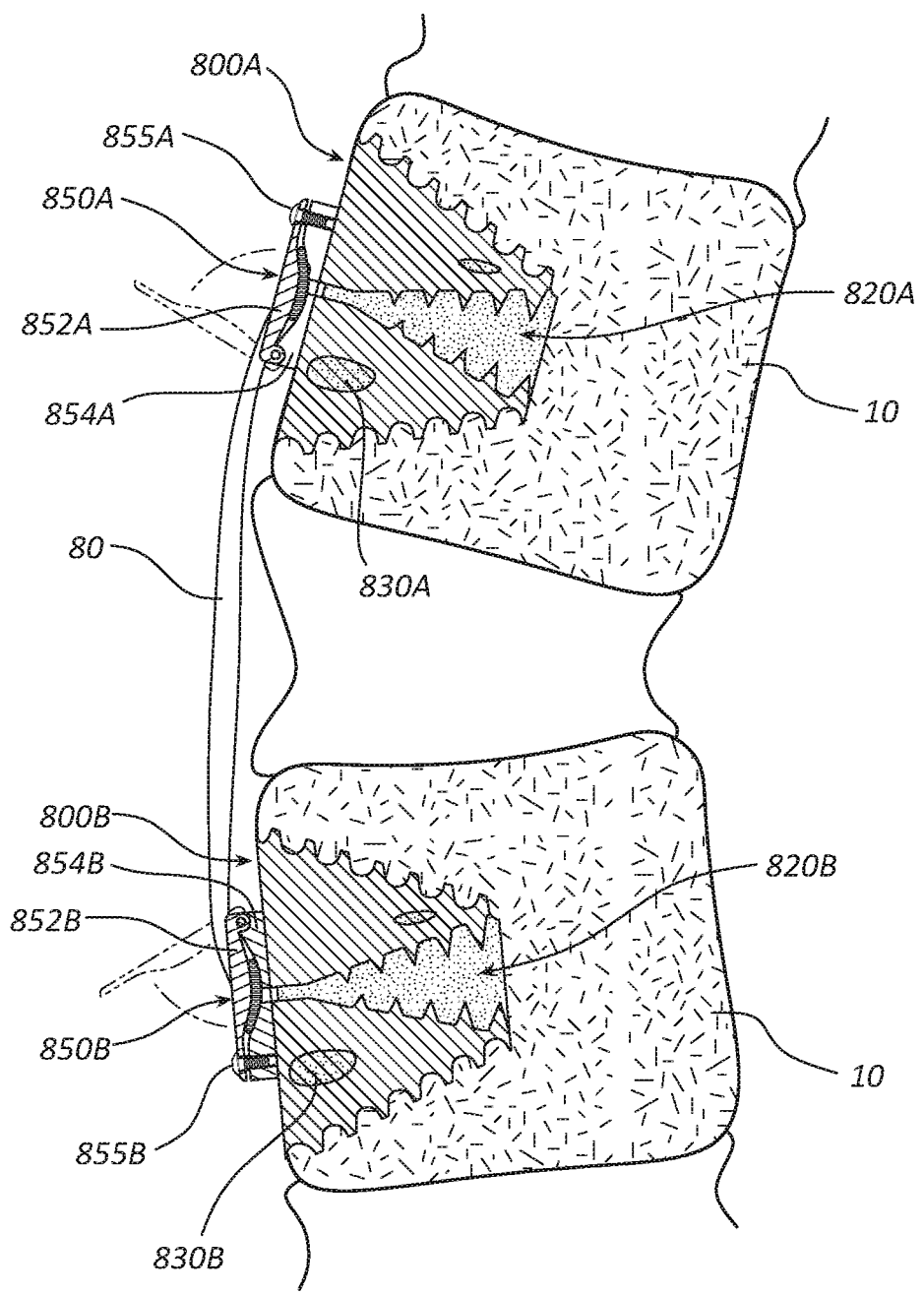
FIG. 8 is a cross-sectional view of a system for spinal deformity correction according to other embodiments.

FIG. 8 depicts still another embodiment of a system for spinal deformity correction. This system again comprises two adjacent bone anchors 800A/800B. These bone anchors 800A/800B again preferably comprise inner chambers 820A/820B that comprise thread forms that may differ from the respective exterior thread forms. Also, one or more tunnels 830A/830B and/or other openings may be formed between the exterior of the bone anchors 800A/800B and the interior of the bone anchors 800A/800B, such as between the inner thread forms and the outer thread forms.

Bone anchors 800A/800B each comprises a distinct type of engagement member 850A/850B. More particularly, engagement members 850A/850B each comprises a clamp defined by a base 854A/854B and a lid 852A/852B that is pivotably coupled to base 854A/854B. A fastener 855A/855B may be used to fix the ligament 80, which may comprise a straight (non-loop) ligament). Thus, the ligament 80 may be clamped at one end or position (associated with one of the two bone anchors 800A/800B) and then inserted through the other clamp/engagement member 850, after which a desired force may be applied to the associated vertebral bodies through ligament 80 and then the opposite end or position may be clamped using the other clamp/engagement member 850.

Preferably, the inner surface of the lid 852 and seat/base 854 are smooth and define a large surface area so as to distribute the force applied to the ligament 80 along a large surface area of the ligament to avoid damage to the ligament 80, as shown in FIG. 8. In some embodiments, clamping force may be applied gradually to ligament 80 so that ligament 80 may be partially clamped using a first force sufficient to keep the ligament in place but allow the ligament 80 to be pulled through engagement members 850A/850B upon application of a threshold larger force. Thus, ligament 80 may be pulled through the clamp defined by the lid 852 and base 854 and then fastener 855 may be further tightened to apply a second, larger locking force that locks the two anchors 800 in place with the desired restoration force. In some embodiments, non-circular ligaments, such as ovoid ligaments, may be used to further enhance this effect if desired. Engagement members 850A and 850B are additional examples of means for engaging a ligament to impart a force to a vertebral body or other tissue or anatomical feature.

Figure 9:
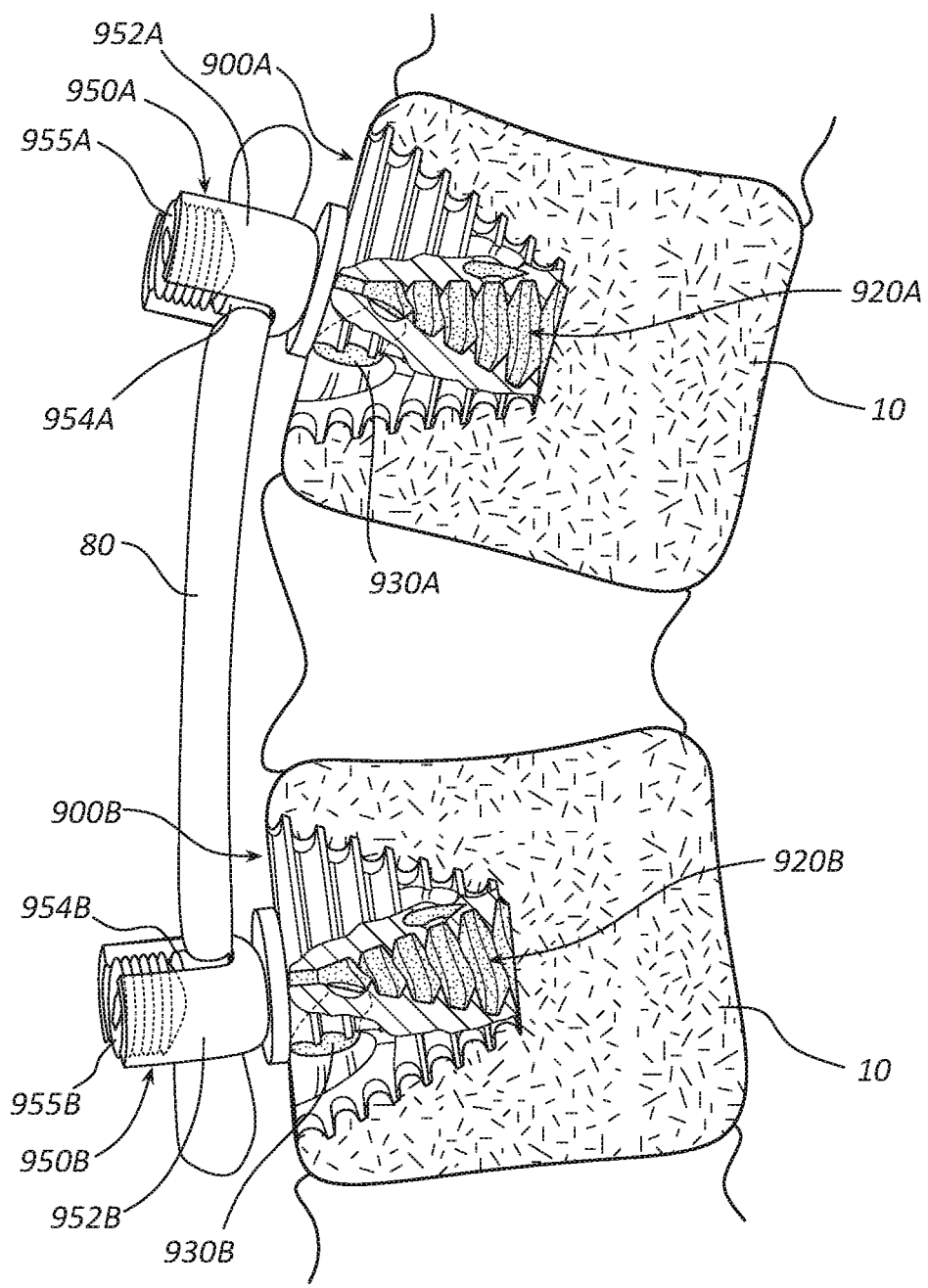
FIG. 9 is a perspective, cutaway view of a system for spinal deformity correction according to still other embodiments.

FIG. 9 depicts yet another embodiment of a system for spinal deformity correction. This system again comprises two adjacent bone anchors 900A/900B that may comprise, or lack if desired, any of the aforementioned features and/or other features available to those of ordinary skill in the art. Thus, bone anchors 900A/900B preferably comprise inner chambers 920A/920B that comprise thread forms that may differ from the respective exterior thread forms, as previously discussed. Also, one or more tunnels 930A/930B and/or other openings may be formed between the exterior of the bone anchors 900A/900B and the interior of the bone anchors 900A/900B, such as between the inner thread forms and the outer thread forms.

Bone anchors 900A/900B each comprises another distinct type of ligament engagement member 950A/950B. More particularly, engagement members 950A/950B each comprises a tulip connector 952A/952B comprising a U-shaped channel configured to receive a ligament 80 or another suitable, preferably flexible, coupling member. Engagement members 950A/950B each further comprises a set screw or cap 955A/955B that is configured to lock the ligament 80 in place within the tulip connector 952A/952B. Due to the flexible nature of the preferred ligaments 80, it may also be desired to provide an intermediary element between the cap 955A/955B and the ligament. Thus, in the depicted embodiment, a saddle 954A/954B is provided. Saddle 954A/954B is configured to distribute the force from the cap 955A/955B about a larger surface area of ligament 80 so as to reduce the possibility of unwanted damage to ligament 80. Notwithstanding the preferable for providing a larger, smoother surface area to reduce damage, it is contemplated that a set screw may be configured to directly contact and lock ligament 80 in place in alternative embodiments.

In some embodiments, the force on ligament 80 may be applied gradually to so that ligament 80 may be partially clamping using a first force sufficient to keep the ligament in place but allow the ligament 80 to be pulled through engagement members 950A/950B upon application of a threshold larger force. Thus, ligament 80 may be pulled through one of the tulip connectors 950 and partially tightened and then later may be further tightened to apply a second, larger locking force that locks the two anchors 900 in place with the desired restoration force. Engagement members 950A and 950B are additional examples of means for engaging a ligament to impart a force to a vertebral body or other tissue or anatomical feature.

Figure 10A:
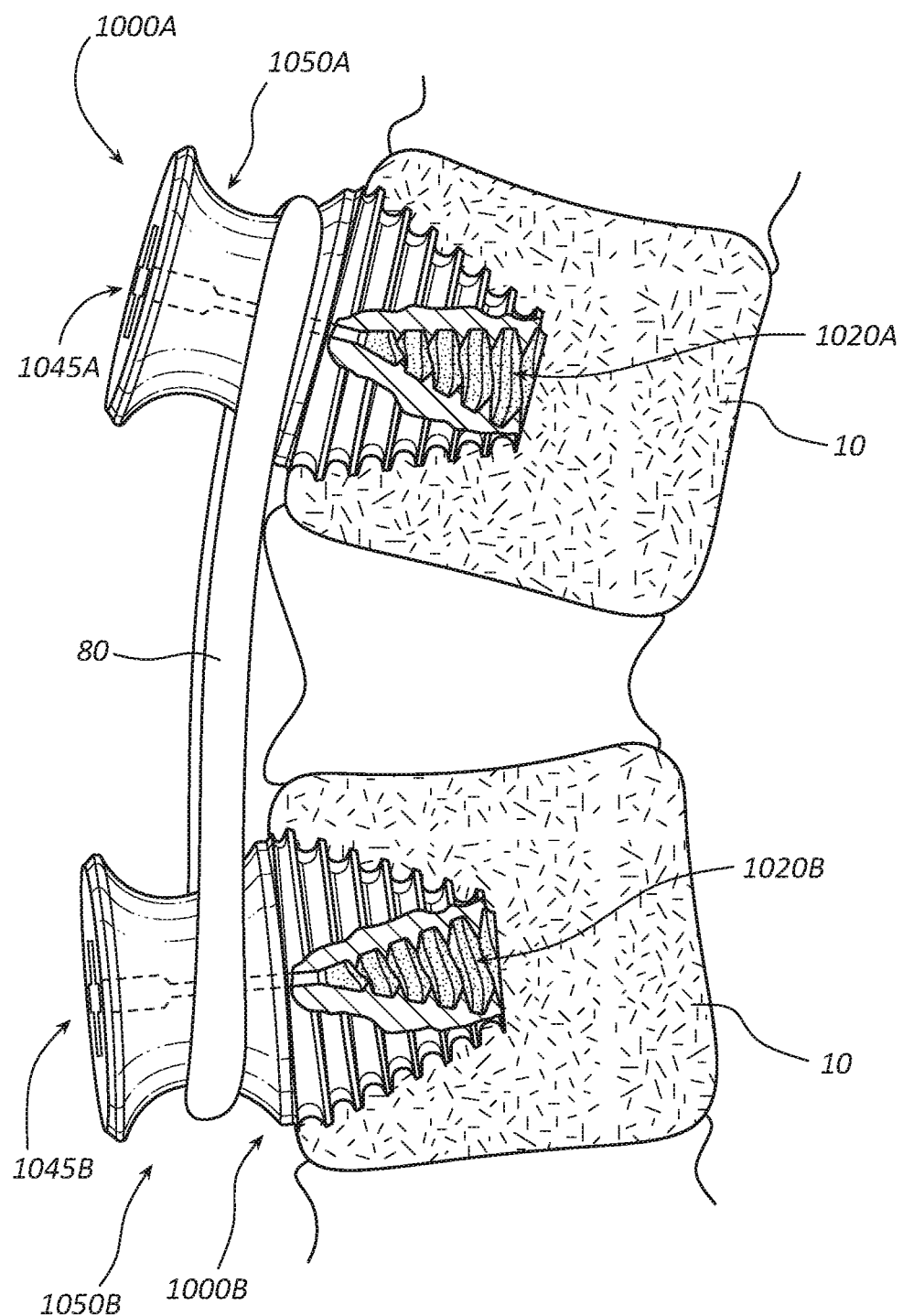
FIG. 10A is a perspective, cutaway view of a system for spinal deformity correction according to further embodiments.
Figure 10B:
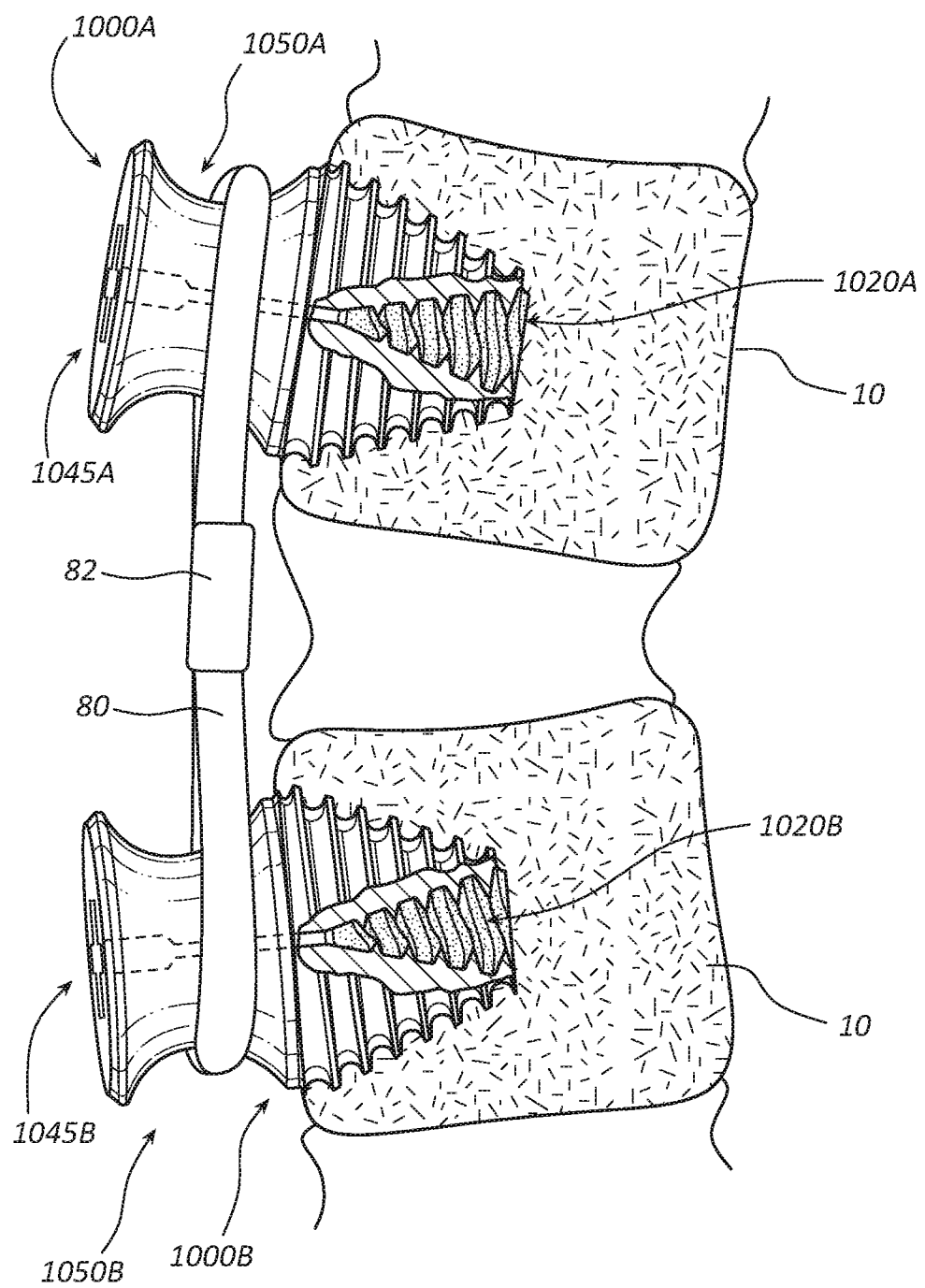
FIG. 10B is a perspective, cutaway view of the system for spinal deformity correction of FIG. 10A following tightening of a loop ligament coupled with two adjacent bone anchors.

FIGS. 10A and 10B depict another embodiment of a system for spinal deformity correction. This system again comprises two or more adjacent bone anchors 1000A/1000B that may comprise, or lack if desired, any of the aforementioned features and/or other features available to those of ordinary skill in the art. Thus, bone anchors 1000A/1000B preferably comprise inner chambers 1020A/1020B that comprise thread forms that may differ from the respective exterior thread forms, as previously discussed. Keyed recesses 1045A/1045B may be provided in a proximal surface of anchors 1000A/1000B to facilitate driving the anchors 1000A/1000B into vertebral bodies 10, as previously discussed.

A loop ligament 80 may be wrapped around respective engagement members 1050A/1050B, as depicted in FIG. 10A. One or more sutures, bands, or other tightening means 82 may then be used to increase the force between anchors 1000A/1000B to apply a restorative force to a spinal column, as depicted in FIG. 10B. As those of ordinary skill in the art will appreciate, any number of such tightening means 82 may be provided as desired to apply forces gradually until the full restorative force desired has been applied.

FIGS. 11A-11D depict various alternative system for spinal deformity correction. Each of the depicted embodiments may comprise similar anchors, including any of the aforementioned bone anchors. Each of the depicted embodiments may further comprise similar engagement members 1150A/1150B that are coupled to the anchors, such as to a proximal end of the anchors, to facilitate application of a restorative or other desired force. However, the systems depicted in these figures comprise a variety of distinct means for increasing the force between adjacent anchors.

Figure 11A:
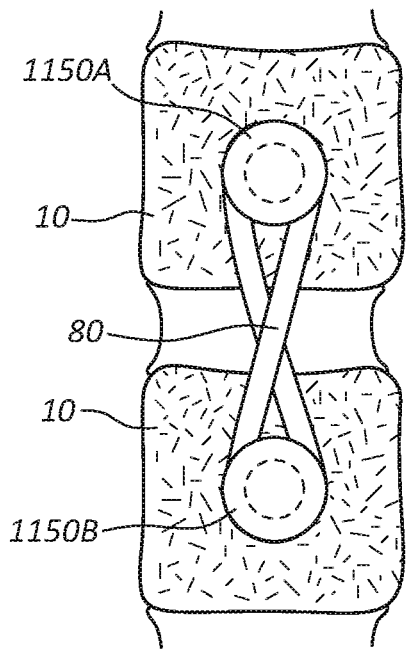
FIGS. 11A-11D depict a variety of alternative means for tightening ligaments to engagement members coupled with bone anchors.

For example, FIG. 11A depicts a loop ligament 80 that is wrapped around adjacent anchors in a figure-8 manner. Thus, the ligament may be coupled to one of the anchors and then rotated any number of times as desired according to the desired force to be applied before being coupled to the opposite anchor.

Figure 11B:
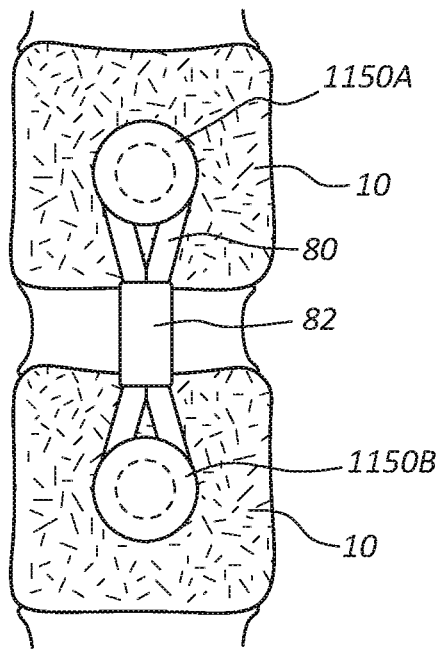

FIG. 11B depicts a system including a means for increasing the force between adjacent anchors that is similar to that depicted in FIG. 10B. Thus, a band 82 may be wrapped around loop ligament 80 at a desired location between adjacent anchors. Band 82 may vary in size according to the desired force to be applied or, as previously mentioned, a plurality of such bands 82 may be used to adjust the force to any desired level.

Figure 11C:
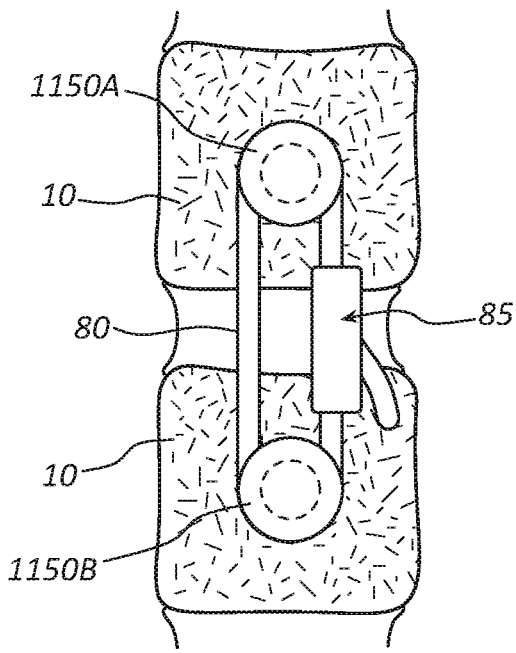

FIG. 11C depicts a straight ligament 80 that may be inserted at opposite ends within a means for increasing the force between adjacent anchors 85 that may comprise, for example, an internal ratchet mechanism that may allow for one end of ligament to be pulled through mechanism 85 to shorten the loop defined thereby without allowing this end to be retracted.

Figure 11D:
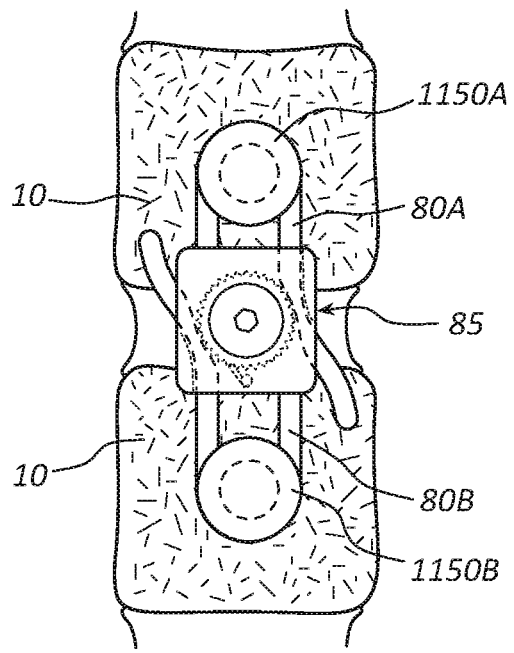

Similarly, FIG. 11D depicts a pair of straight ligaments 80A/80B that may be inserted at opposite ends within another example of a means for increasing the force between adjacent anchors 85. The means for increasing the force 85 depicted in FIG. 11D may allow for one of either of the two opposite ends of ligaments 80A/80B to be pulled through the internal ratcheting mechanism to decrease the length of the defined loop and thereby increase the force being applied to whatever degree of precision required.

Figure 12A:
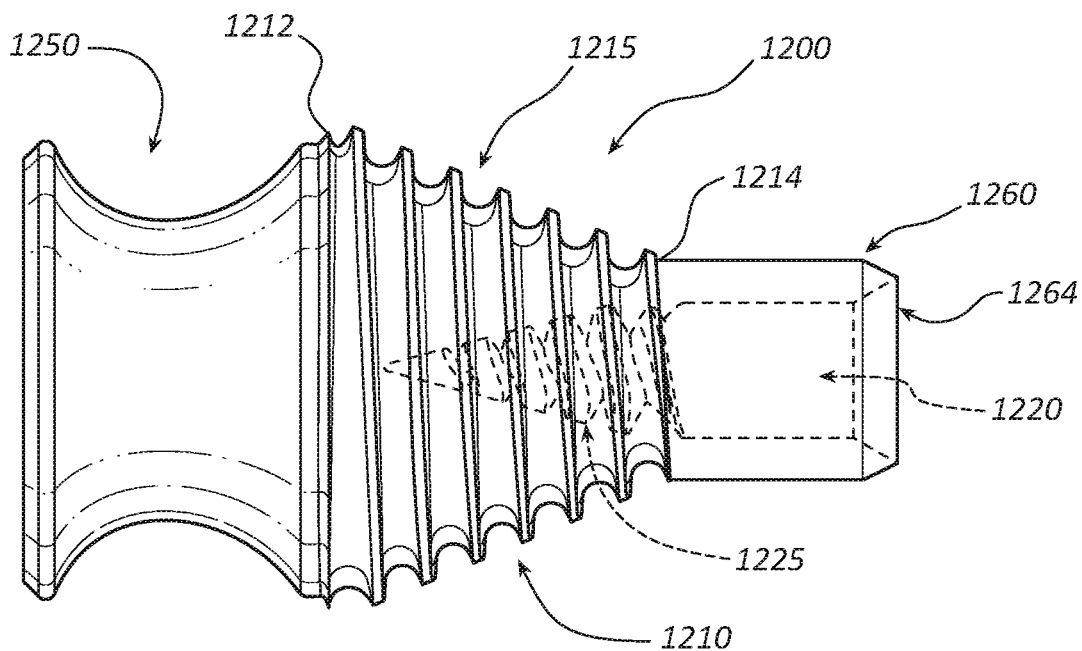
FIG. 12A is a perspective view of a vertebral bone anchor according to additional embodiments.
Figure 12B:
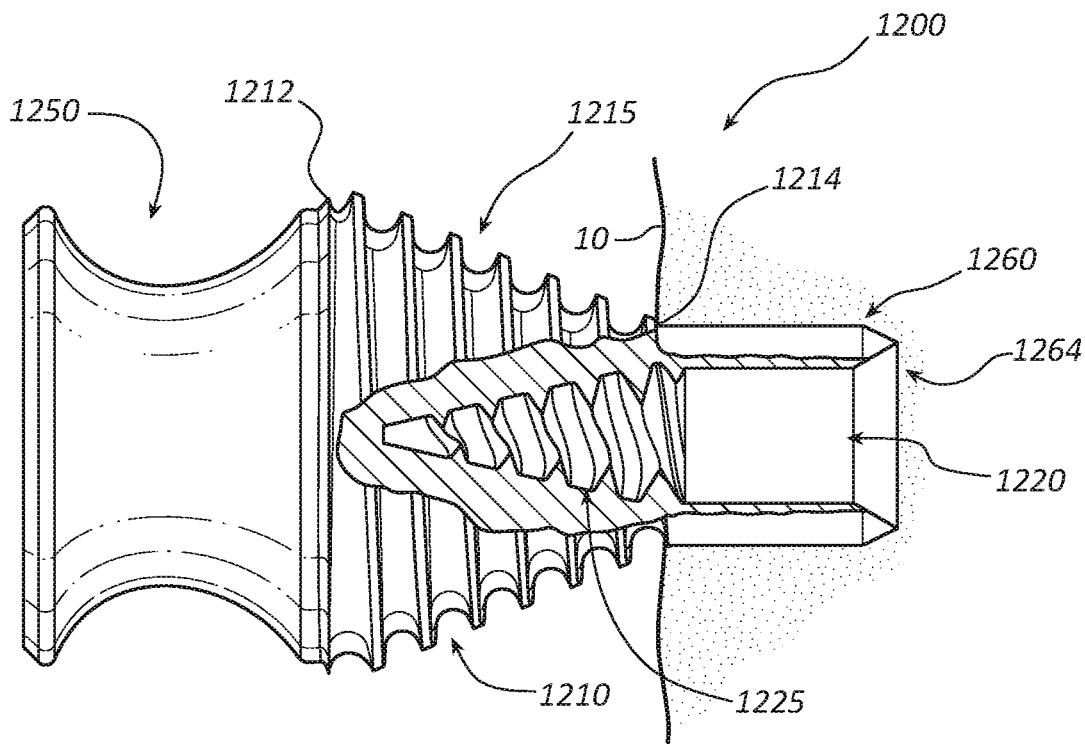
FIG. 12B is a perspective, partial cutaway view of the bone anchor of FIG. 12A being engaged with a vertebral body.

Another example of a bone anchor 1200 is shown in FIGS. 12A and 12B. Bone anchor 1200 is similar to the bone anchors depicted and discussed previously except for the presence of a non-tapering, cylindrical tip 1260. Tip 1260 extends from the distal end 1214 of a tapering portion 1210 (opposite proximal end 1212) and terminates at a preferably sharpened edge 1264 to facilitate penetration into a vertebral body 10 or other bone, as shown in FIG. 12B. In the depicted embodiment, tip 1260 lacks both internal and external threads. As such, bone anchor 1200 may be tamped into the bone before engaging any of the threads. However, in some embodiments, a portion of cylindrical tip 1260, such as preferably a proximal portion, may comprise internal and/or external threads.

It can also be seen that tip 1260 comprises an internal chamber 1220 that extends into the tapering portion. In addition, preferably, at least the proximal portion of chamber 1220 tapers or otherwise varies in size in a direction opposite to the taper of the exterior surface of bone anchor 1200. As previously described, this may allow for bone entering chamber 1220 to be compacted as the anchor 1200 is driven into the bone. In the depicted embodiment, chamber 1220 is cylindrical in shape, similar to the outer surface of tip 1260, along tip 1260 and the reverse tapering of chamber 1220 begins at, or at least substantially at, the distal end 1214 of the tapering section 1210. However, this need not be the case in all embodiments. Indeed, the reverse tapering or other decrease in size of the chamber 1220 from the distal to the proximal end may begin within the cylindrical/non-tapering tip 1260 or may begin proximally of the distal end 1214 of the tapering section.

Otherwise, bone anchor 1200 may be similar to the other anchors depicted in other drawings. For example, the tapering section 1210 may comprise an external thread form 1215 and at least a portion of the inner chamber 1220 may comprise an internal thread form 1225. In some embodiments, the external thread form 1215 may differ from the internal thread form 1225 in one or more ways so as to provide a differential in force between forces generated by the external thread form 1215 on bone adjacent thereto and forces generated by the inner thread form 1225 on bone adjacent thereto. For example, the inner and outer thread forms differ from one another in thread depth, thread direction, number of starts, angle, pitch diameter, major diameter, and/or minor diameter. The internal and/or external thread forms may also vary between their respective proximal and distal ends. In some such embodiments, the internal and/or external thread forms may vary in ways that are different from one another, such as varying along their respective lengths in opposite directions, for example.

Bone anchor 1200 may further comprise an engagement member 1250 for engaging ligaments or other engagement bands, as previously mentioned. One or more of the other features previously described, such as a central cannulation, a keyed feature to facilitate engagement with a driver or other suitable instrument for driving the anchor 1200 into a vertebral body 10 or other tissue, and/or one or more tunnels and/or openings that extend from the exterior surface of anchor 1200 to the inner chamber 1220 may also be provided if desired/useful.

As shown in FIG. 12B, once the non-tapering tip 1260 has been tamped or otherwise inserted into the vertebral body 10, external threads 1215 may be engaged and bone anchor 1200 may be advanced further into the vertebral body 10 by rotation of bone anchor 1200.

Figure 13A:
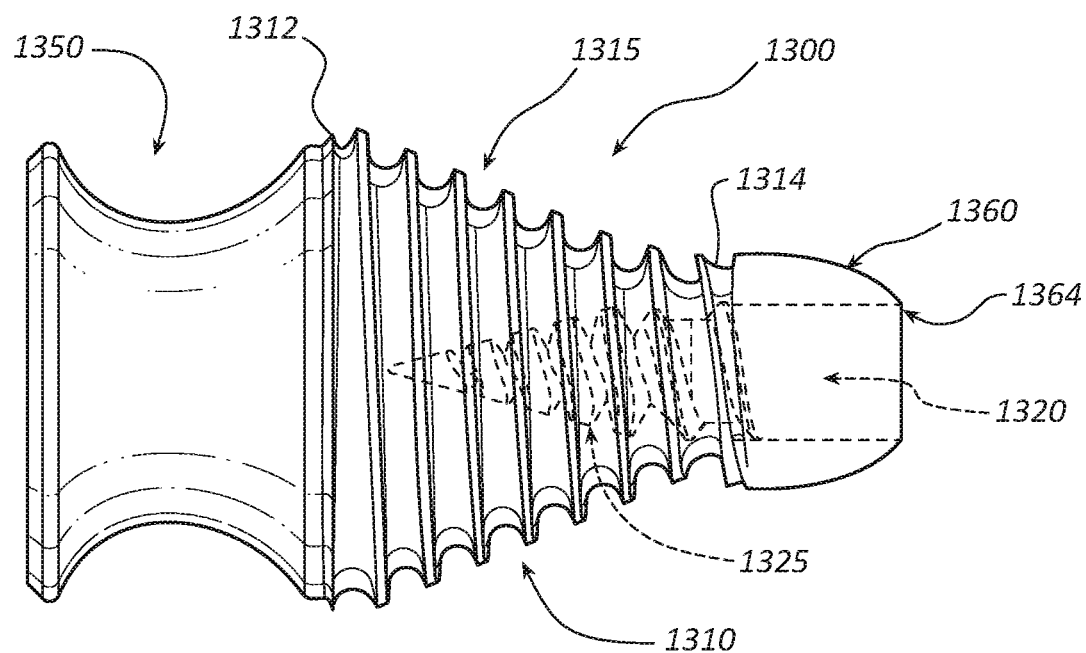
FIG. 13A is a perspective view of a vertebral bone anchor according to further embodiments.
Figure 13B:
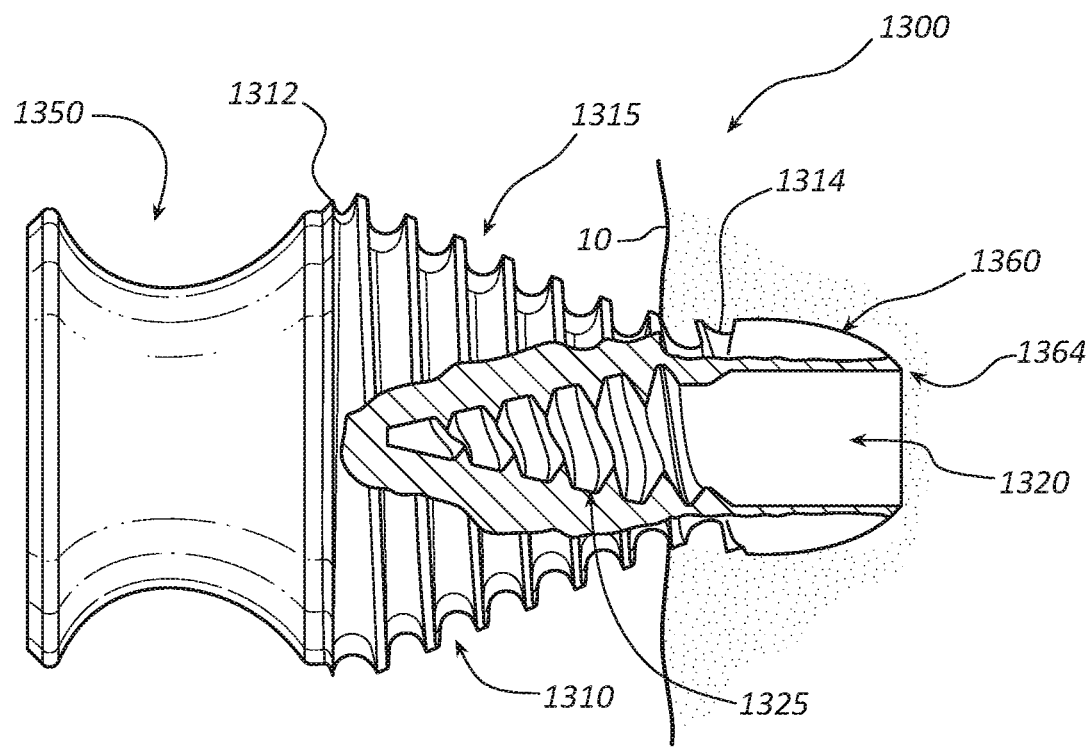
FIG. 13B is a perspective, partial cutaway view of the bone anchor of FIG. 13A being engaged with a vertebral body.

Still another example of a bone anchor 1300 is shown in FIGS. 13A and 13B. Bone anchor 1300 is similar to the bone anchors depicted and discussed previously except for the presence of a tip 1360 that is curved rather than cylindrical as with bone anchor 1200. Tip 1360 extends from the distal end 1314 of a tapering portion 1310 (opposite proximal end 1312) and terminates at a preferably sharpened edge 1364 to facilitate penetration into a vertebral body 10 or other bone, as shown in FIG. 13B. In the depicted embodiment, tip 1360 lacks both internal and external threads. As such, bone anchor 1300 may be tamped into the bone before engaging any of the threads. However, in some embodiments, a portion of cylindrical tip 1360, such as preferably a proximal portion, may comprise internal and/or external threads.

For example, as discussed below in connection with bone anchor 1400, it may be desired in alternative embodiments to begin external thread form 1315 along a proximal portion of tip 1360. As an even more specific example, it may be desired in some embodiments to form threads, which may extend into thread form 1315 continuously in some such embodiments, beginning at or at least substantially at a midpoint of tip 1360 and/or at or at least substantially at the apex of the curve of tip 1360 (the point of the curve furthest from the central axis of the bone anchor 1300).

Tip 1360 further comprises an internal chamber 1320 that extends into the tapering portion. In addition, preferably, at least the proximal portion of chamber 1320 tapers or otherwise varies in size in a direction opposite to the taper of the exterior surface of bone anchor 1300. As previously described, this may allow for bone entering chamber 1320 to be compacted as the anchor 1300 is driven into the bone. In the depicted embodiment, chamber 1320 is cylindrical in shape along tip 1360, similar to the outer surface of tip 1360, and the reverse tapering of chamber 1320 begins at, or at least substantially at, the distal end 1314 of the tapering section 1310. However, this need not be the case in all embodiments. Indeed, the reverse tapering or other decrease in size of the chamber 1320 from the distal to the proximal end may begin within the bowed tip 1360 or may begin proximally of the distal end 1314 of the tapering section. As another alternative, the reverse tapering or other beginning of a decrease in size of the chamber 1320 from distal to proximal may begin at the point at which the external threads begin, which may, as described above, coincide, or at least substantially coincide, with the apex of the curve and/or the midpoint of the tip 1360. In alternative embodiments, tip 1360 may taper to define a conical section rather than a bowed/curved section.

Otherwise, bone anchor 1300 may be similar to the other anchors depicted in other drawings. For example, the tapering section 1310 may comprise an external thread form 1315 and at least a portion of the inner chamber 1320 may comprise an internal thread form 1325. In some embodiments, the external thread form 1315 may differ from the internal thread form 1325 in one or more ways so as to provide a differential in force between forces generated by the external thread form 1315 on bone adjacent thereto and forces generated by the inner thread form 1325 on bone adjacent thereto in any of the ways previously described.

Bone anchor 1300 may further comprise an engagement member 1350 for engaging ligaments or other engagement bands, as previously mentioned. One or more of the other features previously described, such as a central cannulation, a keyed feature to facilitate engagement with a driver or other suitable instrument for driving the anchor 1300 into a vertebral body 10 or other tissue, and/or one or more tunnels and/or openings that extend from the exterior surface of anchor 1300 to the inner chamber 1320 may also be provided if desired/useful.

As shown in FIG. 13B, once the tip 1360 has been tamped or otherwise inserted into the vertebral body 10, external threads 1315 may be engaged and bone anchor 1300 may be advanced further into the vertebral body 10 by rotation of bone anchor 1300, as previously described.

Still another example of a bone anchor 1300 is shown in FIGS. 13A and 13B. Bone anchor 1300 is similar to the bone anchors depicted and discussed previously except for the presence of a tip 1360 that is curved rather than cylindrical as with bone anchor 1200. Tip 1360 extends from the distal end 1314 of a tapering portion 1310 (opposite proximal end 1312) and terminates at a preferably sharpened edge 1364 to facilitate penetration into a vertebral body 10 or other bone, as shown in FIG. 13B. In the depicted embodiment, tip 1360 lacks both internal and external threads. As such, bone anchor 1300 may be tamped into the bone before engaging any of the threads. However, in some embodiments, a portion of cylindrical tip 1360, such as preferably a proximal portion, may comprise internal and/or external threads.

For example, as discussed below in connection with bone anchor 1400, it may be desired in alternative embodiments to begin external thread form 1315 along a proximal portion of tip 1360. As an even more specific example, it may be desired in some embodiments to form threads, which may extend into thread form 1315 continuously in some such embodiments, beginning at or at least substantially at a midpoint of tip 1360 and/or at or at least substantially at the apex of the curve of tip 1360 (the point of the curve furthest from the central axis of the bone anchor 1300).

Tip 1360 further comprises an internal chamber 1320 that extends into the tapering portion. In addition, preferably, at least the proximal portion of chamber 1320 tapers or otherwise varies in size in a direction opposite to the taper of the exterior surface of bone anchor 1300. As previously described, this may allow for bone entering chamber 1320 to be compacted as the anchor 1300 is driven into the bone. In the depicted embodiment, chamber 1320 is cylindrical in shape along tip 1360, similar to the outer surface of tip 1360, and the reverse tapering of chamber 1320 begins at, or at least substantially at, the distal end 1314 of the tapering section 1310. However, this need not be the case in all embodiments. Indeed, the reverse tapering or other decrease in size of the chamber 1320 from the distal to the proximal end may begin within the bowed tip 1360 or may begin proximally of the distal end 1314 of the tapering section. As another alternative, the reverse tapering or other beginning of a decrease in size of the chamber 1320 from distal to proximal may begin at the point at which the external threads begin, which may, as described above, coincide, or at least substantially coincide, with the apex of the curve and/or the midpoint of the tip 1360.

Otherwise, bone anchor 1300 may be similar to the other anchors depicted in other drawings. For example, the tapering section 1310 may comprise an external thread form 1315 and at least a portion of the inner chamber 1320 may comprise an internal thread form 1325. In some embodiments, the external thread form 1315 may differ from the internal thread form 1325 in one or more ways so as to provide a differential in force between forces generated by the external thread form 1315 on bone adjacent thereto and forces generated by the inner thread form 1325 on bone adjacent thereto in any of the ways previously described.

Bone anchor 1300 may further comprise an engagement member 1350 for engaging ligaments or other engagement bands, as previously mentioned. One or more of the other features previously described, such as a central cannulation, a keyed feature to facilitate engagement with a driver or other suitable instrument for driving the anchor 1300 into a vertebral body 10 or other tissue, and/or one or more tunnels and/or openings that extend from the exterior surface of anchor 1300 to the inner chamber 1320 may also be provided if desired/useful.

As shown in FIG. 13B, once the tip 1360 has been tamped or otherwise inserted into the vertebral body 10, external threads 1315 may be engaged and bone anchor 1300 may be advanced further into the vertebral body 10 by rotation of bone anchor 1300, as previously described.

Figure 14A:
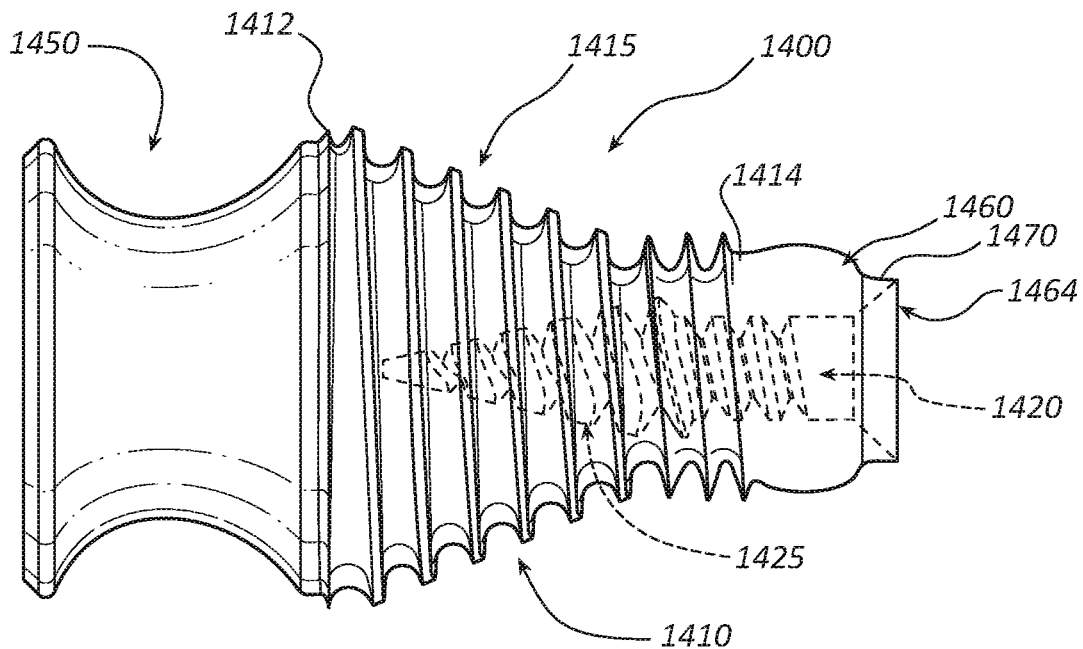
FIG. 14A is a perspective view of a vertebral bone anchor according to still other embodiments.
Figure 14B:
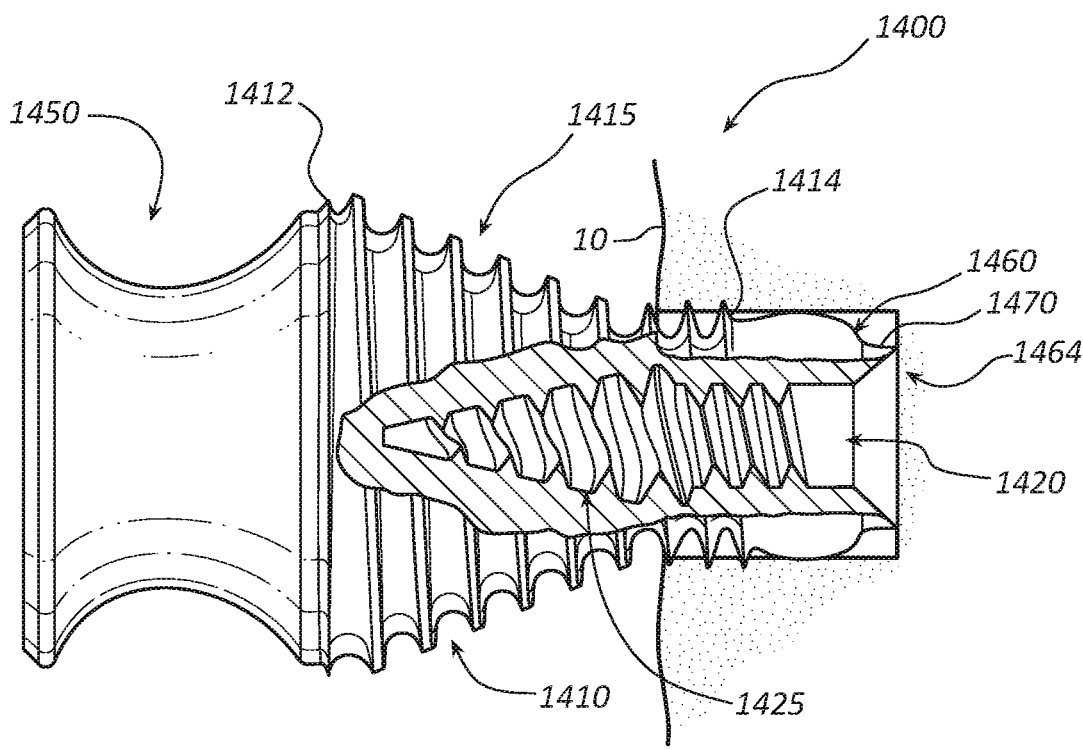
FIG. 14B is a perspective, partial cutaway view of the bone anchor of FIG. 14A being engaged with a vertebral body.

A final example of a bone anchor 1400 according to still other embodiments is shown in FIGS. 14A and 14B. Bone anchor 1400 is similar to the bone anchors depicted and discussed previously except for the configuration of the tip, which includes a distal end portion 1470 that is cylindrical and an adjacent curved/bowed portion 1460. Cylindrical tip 1470 may again comprise a sharp edge to facilitate penetration/tamping into a vertebral body or other bone. The adjacent bowed/curved portion 1460 may serve one or more useful functions such as providing inhibiting forces to slow down the tamping of bone anchor 1400 prior to engagement of threads, external and/or internal, with the adjacent bone. This may allow for creation of an initial circular channel with an expansion created by the bowed/curved portion 1460 (or similar cylindrical section) wide enough to allow the initial thread start from external thread form 1415 to enter below the cortical wall and easily engage the cancellous bone underneath the cortical wall for simple initial screw purchase and advancement.

As mentioned above in connection with section 1360, section 1460 may, in alternative embodiments, comprise a tapering and/or conical section rather than a curved/bowed section, which may provide similar benefits by, for example, slowing the rate of tamping by providing an opposing force after tip 1470 has entered the bone.

Bowed/curved section 1460 extends from the distal end 1414 of tapering portion 1410 (opposite proximal end 1412). In the depicted embodiment, tip section 1460 comprises external threads that preferably begin at or near the apex of the curvature, as described above, and may extend cylindrically for a short distance, after which they may taper along the tapered section 1410 to form a part of external thread form 1415.

Tip 1460 further comprises an internal chamber 1420 that extends into the tapering portion. In addition, preferably, at least the proximal portion of chamber 1420 tapers or otherwise varies in size in a direction opposite to the taper of the exterior surface of bone anchor 1400. Again, this may allow for bone entering chamber 1420 to be compacted as the anchor 1400 is driven into the bone. In the depicted embodiment, chamber 1420 is cylindrical in shape along the tip portions and the reverse tapering of chamber 1420 begins at, or at least substantially at, the distal end 1414 of the tapering section 1410.

However, this need not be the case in all embodiments. Indeed, the reverse tapering or other decrease in size of the chamber 1420 from the distal to the proximal end may begin within the bowed portion 1460, within the cylindrical tip portion 1470, or may begin proximally of the distal end 1414 of the tapering section. As another alternative, the reverse tapering or other beginning of a decrease in size of the chamber 1420 from distal to proximal may begin at the point at which the external threads begin, which may, as described above, coincide, or at least substantially coincide, with the apex of the curve and/or the midpoint of the bowed portion 1460.

Internal threads may also be formed within chamber 1420. For example, in the depicted embodiment, the internal thread form 1425 begins at or near the beginning of the external thread form 1415. Of course, this need not be the case in all embodiments. Indeed, the internal thread form may begin proximally or distally of the external thread form in alternative embodiments.

In the depicted embodiment, the internal thread form 1425 comprises a non-tapering section that may overlap with the bowed section 1460. In some cases, the internal thread form 1425 may coincide identically or at least substantially identically with the bowed section 1460 and/or tip 1470. The internal thread form 1425 may then reverse taper along the tapering section of the inner chamber 1420.

In some embodiments, the external thread form 1415 may differ from the internal thread form 1425 in one or more ways so as to provide a differential in force between forces generated by the external thread form 1415 on bone adjacent thereto and forces generated by the inner thread form 1425 on bone adjacent thereto in one or more of the ways described elsewhere herein.

Bone anchor 1300 may further comprise an engagement member 1350 for engaging ligaments or other engagement bands, as previously mentioned. One or more of the other features previously described, such as a central cannulation, a keyed feature to facilitate engagement with a driver or other suitable instrument for driving the anchor 1300 into a vertebral body 10 or other tissue, and/or one or more tunnels and/or openings that extend from the exterior surface of anchor 1300 to the inner chamber 1320 may also be provided if desired/useful.

As shown in FIG. 14B, once the tip (made up of tip portions 1460 and 1470) has been tamped or otherwise inserted into the vertebral body 10, external threads 1415 may be engaged and bone anchor 1400 may be advanced further into the vertebral body 10 by rotation of bone anchor 1400, as previously described.

It will be understood by those having skill in the art that changes may be made to the details of the above-described embodiments without departing from the underlying principles presented herein. Any suitable combination of various embodiments, or the features thereof, is contemplated.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Throughout this specification, any reference to "one embodiment," "an embodiment," or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, inventive aspects lie in a combination of fewer than all features of any single foregoing disclosed embodiment. It will be apparent to those having skill in the art that changes may be made to the details of the above-described embodiments without departing from the underlying principles set forth herein.

Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. The scope of the present invention should, therefore, be determined only by the following claims. The scope of the present invention should, therefore, be determined only by the following claims.

The invention claimed is:

1. A threaded bone anchor configured for engagement with a vertebral body, comprising:
   a first section comprising an at least substantially conical shape in cross section;
   a second section comprising an at least substantially cylindrical shape in cross section, wherein the second section is positioned distal of the first section and forms a tip of the bone anchor;
   an outer thread form formed on an outer surface of the bone anchor;
   an inner chamber open at a distal end of the threaded bone anchor; and
   an inner thread form on an inner surface of the bone anchor within the inner chamber.

2. The bone anchor of claim 1, further comprising a third section comprising a cross-sectional width in a direction at least substantially perpendicular to an elongated axis of the bone anchor, wherein the cross-sectional width is maximal between opposing ends of the third section.

3. The bone anchor of claim 2, wherein the third section is positioned in between the first section and the second section.

4. The bone anchor of claim 2, wherein the third section comprises an outer surface having a convex, curved shape.

5. The bone anchor of claim 4, wherein the third section comprises an outer thread form beginning at least substantially at a point of maximal width of the third section.

6. The bone anchor of claim 1, wherein the inner thread form differs from the outer thread form so as to provide a differential in force between forces generated by the outer thread form on vertebral bone adjacent to the outer thread form and forces generated by the inner thread form on vertebral bone within the inner chamber.

7. The bone anchor of claim 1, wherein the second section lacks outer threads.

8. The bone anchor of claim 7, wherein the second section further lacks inner threads.

9. The bone anchor of claim 1, wherein the second section comprises a sharp edge configured to facilitate penetration into a vertebral body.

10. A threaded bone anchor configured for engagement with a vertebral body, comprising:
    a tapered section comprising an outer thread form; and
    an inner chamber comprising an inner thread form, wherein the inner chamber comprises a proximal end and a distal end, wherein the inner chamber decreases in size, at least in part, between the distal end and the proximal end, and wherein the inner thread form differs from the outer thread form so as to provide a differential in force between forces generated by the outer thread form on vertebral bone adjacent to the outer thread form and forces generated by the inner thread form on vertebral bone within the inner chamber.

11. The bone anchor of claim 10, wherein the inner and outer thread forms differ from one another in at least one of thread depth, thread direction, number of starts, angle, pitch diameter, major diameter, and minor diameter.

12. The bone anchor of claim 11, wherein the inner thread form comprises a larger thread depth than the outer thread form.

13. The bone anchor of claim 10, wherein the inner chamber tapers, at least in part, from a proximal portion of the bone anchor to a distal portion of the bone anchor to define a wider bone anchor width at a proximal portion of a tapering section of the bone anchor than at a distal portion of the tapering section.

14. The bone anchor of claim 13, wherein the inner chamber tapers along an entire length of the inner chamber.

15. The bone anchor of claim 10, further comprising a non-tapered section positioned at a distal end of the bone anchor.

16. The bone anchor of claim 15, wherein the non-tapered section lacks threads.

17. A bone anchor configured for engagement with a vertebral body, comprising:
    an outer surface configured to engage vertebral bone and extending along a longitudinal axis of the bone anchor, wherein the outer surface tapers, at least in part, from a proximal portion of the bone anchor to a distal portion of the bone anchor to define a wider bone anchor width at a proximal portion of a tapering section of the bone anchor than at a distal portion of the tapering section;
    an inner chamber configured to engage and compact vertebral bone therein, wherein the inner chamber tapers in a direction opposite a direction in which the outer surface tapers such that at least a portion of the inner chamber is wider at a distal portion of the inner chamber than an adjacent proximal portion of the inner chamber; and
    an engagement member positioned at a proximal end of the bone anchor, wherein the engagement member is configured to engage a flexible member to allow for coupling of the bone anchor with an adjacent bone anchor.

18. The bone anchor of claim 17, wherein the inner chamber comprises an inner thread form.

19. The bone anchor of claim 18, wherein the outer surface comprises an outer thread form, and wherein the inner thread form of the inner chamber differs from the outer thread form of the outer chamber so as to provide a differential in force between forces generated by the outer thread form on vertebral bone adjacent to the outer thread form and forces generated by the inner thread form on vertebral bone within the inner chamber.

20. The bone anchor of claim 17, further comprising a cylindrical section forming a tip of the bone anchor, wherein the tip is configured to facilitate penetration into a vertebral body.

* * * * *